United States Patent
Bess et al.

(10) Patent No.: US 10,758,274 B1
(45) Date of Patent: Sep. 1, 2020

(54) SPINAL FIXATION CONSTRUCTS AND RELATED METHODS

(71) Applicant: NuVasive, Inc., San Diego, CA (US)

(72) Inventors: Robert Shay Bess, Littleton, CO (US); Regis W. Haid, Atlanta, GA (US); Frank Schwab, New York, NY (US); Christopher Shaffrey, Charlottesville, VA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 14/703,852

(22) Filed: May 4, 2015

Related U.S. Application Data

(60) Provisional application No. 61/988,066, filed on May 2, 2014.

(51) Int. Cl.
 *A61B 17/70* (2006.01)
(52) U.S. Cl.
 CPC ...... *A61B 17/7001* (2013.01); *A61B 17/7019* (2013.01); *A61B 17/7022* (2013.01); *A61B 17/7023* (2013.01); *A61B 17/7032* (2013.01); *A61B 17/7035* (2013.01); *A61B 17/7043* (2013.01)
(58) Field of Classification Search
 CPC . A61B 17/70; A61B 17/7001; A61B 17/7002; A61B 17/7011; A61B 17/7013; A61B 17/7014; A61B 17/7019; A61B 17/7022; A61B 17/7026; A61B 17/7031; A61B 17/7032; A61B 17/7035; A61B 17/7037; A61B 17/7038; A61B 17/7046; A61B 17/7056; A61B 17/842; A61B 17/8605
 See application file for complete search history.

(56) References Cited

U.S. PATENT DOCUMENTS

| | | | |
|---|---|---|---|
| 4,448,191 A | 5/1984 | Rodnyansky et al. |
| 4,641,636 A | 2/1987 | Cotrel |
| 4,743,260 A | 5/1988 | Burton |
| 5,000,165 A | 3/1991 | Watanabe |
| 5,263,954 A | 11/1993 | Schlapfer et al. |
| 5,267,999 A | 12/1993 | Olerud |
| 5,271,461 A | 12/1993 | Decker et al. |
| 5,282,863 A | 2/1994 | Burton |

(Continued)

FOREIGN PATENT DOCUMENTS

| CN | 103767778 | 5/2014 |
|---|---|---|
| DE | 2821678 | 11/1979 |

(Continued)

*Primary Examiner* — Lynnsy M Summitt

(57) ABSTRACT

This disclosure describes a variety of transitional or terminal components that may be implanted as part of a spinal fixation construct to decrease the potential for subsequent development of junctional disease. The fixation construct may extend any number of levels from a single level construct to a long construct spanning multiple spinal levels and multiple spinal regions from the lumbosacral to cervical regions, and with any variety of combination of anchors, rods, and connectors. Terminal and/or transitional components may be utilized at the caudal and or cephalad ends of the fixation construct to reduce stresses endured by the construct adjacent pathology and prevent or reduce incidence and degree of junctional disease.

19 Claims, 27 Drawing Sheets

(56) References Cited

U.S. PATENT DOCUMENTS

| | | | |
|---|---|---|---|
| 5,375,823 A | 12/1994 | Navas | |
| 5,387,213 A | 2/1995 | Breard et al. | |
| 5,415,661 A | 5/1995 | Holmes | |
| 5,480,401 A | 1/1996 | Navas | |
| 5,540,668 A | 7/1996 | Wilson, Jr. et al. | |
| 5,540,703 A * | 7/1996 | Barker, Jr. | A61L 17/04 |
| | | | 289/1.2 |
| 5,562,660 A | 10/1996 | Grob | |
| 5,584,832 A | 12/1996 | Schlapfer | |
| 5,593,408 A | 1/1997 | Gayet et al. | |
| 5,632,744 A | 5/1997 | Campbell, Jr. | |
| 5,672,175 A | 9/1997 | Martin | |
| 5,810,818 A | 9/1998 | Errico et al. | |
| RE36,221 E | 6/1999 | Breard et al. | |
| 5,961,516 A | 10/1999 | Graf | |
| 6,022,350 A | 2/2000 | Ganem | |
| 6,099,528 A | 8/2000 | Saurat | |
| 6,241,730 B1 | 6/2001 | Alby | |
| 6,290,700 B1 | 9/2001 | Schmotzer | |
| 6,293,949 B1 | 9/2001 | Justis et al. | |
| 6,402,750 B1 | 6/2002 | Atkinson et al. | |
| 6,440,169 B1 | 8/2002 | Elberg et al. | |
| 6,551,320 B2 * | 4/2003 | Lieberman | A61B 17/7022 |
| | | | 606/263 |
| 6,645,207 B2 | 11/2003 | Dixon et al. | |
| 6,761,719 B2 | 7/2004 | Justis et al. | |
| 6,770,075 B2 | 8/2004 | Howland | |
| 6,783,527 B2 | 8/2004 | Drewry et al. | |
| 6,835,207 B2 | 12/2004 | Zacouto et al. | |
| 6,966,910 B2 | 11/2005 | Ritland | |
| 6,986,771 B2 | 1/2006 | Paul et al. | |
| 6,989,011 B2 | 1/2006 | Paul et al. | |
| 7,018,379 B2 | 3/2006 | Drewry et al. | |
| 7,377,921 B2 | 5/2008 | Studer et al. | |
| 7,563,274 B2 | 7/2009 | Justis et al. | |
| 7,678,139 B2 | 3/2010 | Garamszegi et al. | |
| 7,806,914 B2 | 10/2010 | Boyd et al. | |
| 7,815,663 B2 | 10/2010 | Trieu | |
| 7,824,430 B2 * | 11/2010 | Allard | A61B 17/7022 |
| | | | 606/279 |
| 7,828,825 B2 * | 11/2010 | Bruneau | A61B 17/7031 |
| | | | 606/257 |
| 7,862,588 B2 * | 1/2011 | Abdou | A61B 17/8685 |
| | | | 606/246 |
| 7,875,059 B2 | 1/2011 | Patterson et al. | |
| 7,901,435 B2 | 3/2011 | Slivka et al. | |
| 7,967,848 B2 * | 6/2011 | Abdelgany | A61B 17/7037 |
| | | | 606/266 |
| 8,012,182 B2 | 9/2011 | Couedic et al. | |
| 8,057,516 B2 * | 11/2011 | Zylber | A61B 17/7005 |
| | | | 606/254 |
| 8,137,384 B2 | 3/2012 | Heiges et al. | |
| 8,177,816 B2 * | 5/2012 | Schwab | A61B 17/7032 |
| | | | 606/246 |
| 8,292,934 B2 | 10/2012 | Justis et al. | |
| 8,317,830 B2 * | 11/2012 | Molz | A61B 17/7032 |
| | | | 606/246 |
| 8,333,792 B2 | 12/2012 | Winslow et al. | |
| 8,419,773 B2 | 4/2013 | Biedermann et al. | |
| 8,430,912 B2 | 4/2013 | Veldman et al. | |
| 8,449,574 B2 | 5/2013 | Biedermann et al. | |
| 8,523,915 B2 * | 9/2013 | Van Nortwick | A61B 17/7001 |
| | | | 606/270 |
| 8,523,922 B2 * | 9/2013 | May | A61B 17/7032 |
| | | | 606/300 |
| 8,562,652 B2 * | 10/2013 | Biedermann | A61B 17/7035 |
| | | | 606/266 |
| 8,641,735 B2 | 2/2014 | Serbousek | |
| 8,657,856 B2 | 2/2014 | Gephart et al. | |
| 8,702,760 B2 | 4/2014 | Pafford et al. | |
| 8,808,330 B2 | 8/2014 | Biedermann | |
| 8,828,058 B2 | 9/2014 | Elsebaie et al. | |
| 8,870,924 B2 * | 10/2014 | Hestad | A61B 17/7032 |
| | | | 606/257 |
| 9,072,546 B2 * | 7/2015 | Trieu | A61B 17/7026 |
| 9,173,685 B2 * | 11/2015 | Lindquist | A61B 17/7049 |
| 9,237,907 B2 * | 1/2016 | Powers | A61B 17/7022 |
| 9,314,285 B2 | 4/2016 | Reisberg | |
| 9,320,542 B2 | 4/2016 | Browne | |
| 9,320,543 B2 * | 4/2016 | Fanger | A61B 17/7005 |
| 9,486,252 B2 | 11/2016 | Mccarthy | |
| 9,597,124 B2 | 3/2017 | McCarthy et al. | |
| 2003/0055427 A1 | 3/2003 | Graf | |
| 2003/0109880 A1 | 6/2003 | Shirado et al. | |
| 2003/0171749 A1 | 9/2003 | Le Couedic et al. | |
| 2003/0220642 A1 | 11/2003 | Freudiger | |
| 2003/0220643 A1 | 11/2003 | Ferree | |
| 2004/0002708 A1 | 1/2004 | Ritland | |
| 2004/0049189 A1 | 3/2004 | Le Couedic et al. | |
| 2004/0049190 A1 | 3/2004 | Biedermann et al. | |
| 2004/0073215 A1 | 4/2004 | Carli | |
| 2004/0143264 A1 | 7/2004 | McAfee | |
| 2004/0225289 A1 | 11/2004 | Biedermann et al. | |
| 2004/0236329 A1 | 11/2004 | Panjabi | |
| 2004/0267260 A1 | 12/2004 | Mack et al. | |
| 2005/0056979 A1 | 3/2005 | Studer et al. | |
| 2005/0065514 A1 | 3/2005 | Studer | |
| 2005/0065516 A1 | 3/2005 | Jahng | |
| 2005/0085815 A1 | 4/2005 | Harms et al. | |
| 2005/0090822 A1 | 4/2005 | DiPoto | |
| 2005/0113927 A1 | 5/2005 | Malek | |
| 2005/0131405 A1 | 6/2005 | Molz, IV et al. | |
| 2005/0143737 A1 | 6/2005 | Pafford et al. | |
| 2005/0143823 A1 | 6/2005 | Boyd et al. | |
| 2005/0149020 A1 | 7/2005 | Jahng | |
| 2005/0154390 A1 | 7/2005 | Biedermann et al. | |
| 2005/0165396 A1 | 7/2005 | Fortin et al. | |
| 2005/0171543 A1 | 8/2005 | Timm et al. | |
| 2005/0177156 A1 | 8/2005 | Timm et al. | |
| 2005/0177157 A1 | 8/2005 | Jahng | |
| 2005/0182401 A1 | 8/2005 | Timm et al. | |
| 2005/0203514 A1 | 9/2005 | Jahng et al. | |
| 2005/0203516 A1 | 9/2005 | Biedermann et al. | |
| 2005/0203517 A1 | 9/2005 | Jahng et al. | |
| 2005/0203519 A1 | 9/2005 | Harms et al. | |
| 2005/0209694 A1 | 9/2005 | Loeb | |
| 2005/0216003 A1 | 9/2005 | Biedermann et al. | |
| 2005/0261685 A1 | 11/2005 | Fortin et al. | |
| 2005/0277920 A1 | 12/2005 | Slivka et al. | |
| 2005/0277922 A1 | 12/2005 | Trieu et al. | |
| 2006/0142758 A1 | 6/2006 | Petit | |
| 2006/0142760 A1 | 6/2006 | McDonnell | |
| 2007/0233089 A1 * | 10/2007 | DiPoto | A61B 17/7011 |
| | | | 606/279 |
| 2007/0276384 A1 | 11/2007 | Spratt | |
| 2009/0005815 A1 | 1/2009 | Ely | |
| 2009/0062868 A1 | 3/2009 | Casutt | |
| 2009/0248077 A1 * | 10/2009 | Johns | A61B 17/7011 |
| | | | 606/246 |
| 2009/0264933 A1 | 10/2009 | Carls et al. | |
| 2010/0057126 A1 * | 3/2010 | Hestad | A61B 17/7032 |
| | | | 606/246 |
| 2010/0160967 A1 | 6/2010 | Capozzoli | |
| 2010/0256691 A1 | 10/2010 | Park | |
| 2011/0029018 A1 * | 2/2011 | Carlos | A61B 17/7004 |
| | | | 606/246 |
| 2011/0257687 A1 | 10/2011 | Trieu et al. | |
| 2012/0053640 A1 | 3/2012 | Trieu | |
| 2012/0109202 A1 | 5/2012 | Kretzer et al. | |
| 2012/0116462 A1 * | 5/2012 | Arambula | A61B 17/7037 |
| | | | 606/305 |
| 2012/0290013 A1 | 11/2012 | Simonson | |
| 2013/0072983 A1 | 3/2013 | Lindquist et al. | |
| 2013/0103097 A1 * | 4/2013 | May | A61B 17/7032 |
| | | | 606/305 |
| 2013/0123854 A1 | 5/2013 | Kondrashov et al. | |
| 2013/0218207 A1 * | 8/2013 | Carls | A61B 17/7035 |
| | | | 606/278 |
| 2014/0343612 A1 | 11/2014 | Rezach et al. | |

(56) References Cited

U.S. PATENT DOCUMENTS

| | | | |
|---|---|---|---|
| 2015/0230827 A1* | 8/2015 | Zylber | A61B 17/7019 606/264 |
| 2016/0015430 A1 | 1/2016 | Buttermann | |
| 2016/0183981 A1 | 6/2016 | Schlaepfer et al. | |

FOREIGN PATENT DOCUMENTS

| | | |
|---|---|---|
| DE | 4239716 | 8/1994 |
| DE | 102012104978 | 12/2013 |
| DE | 202012012881 | 5/2014 |
| EP | 0667127 | 8/1995 |
| EP | 0669109 | 8/1995 |
| EP | 0677277 | 10/1995 |
| GB | 2382304 | 5/2003 |
| SU | 1136803 | 1/1985 |
| WO | WO1996015729 | 5/1996 |
| WO | WO2001045576 | 6/2001 |
| WO | WO2002102259 | 12/2002 |
| WO | WO2004024011 | 3/2004 |
| WO | WO2005037150 | 4/2005 |
| WO | WO2009028836 | 3/2009 |
| WO | WO2013182545 | 12/2013 |

* cited by examiner

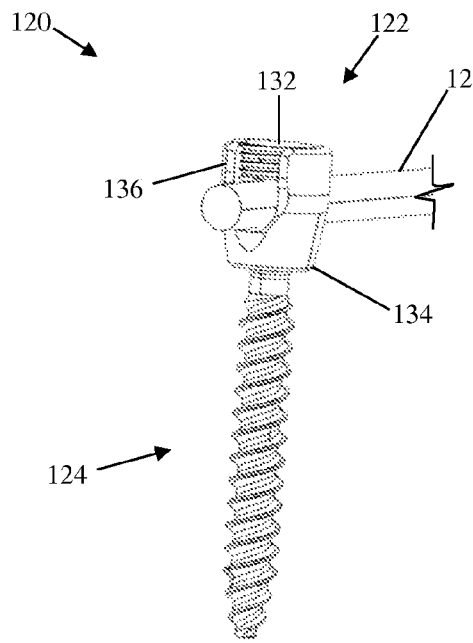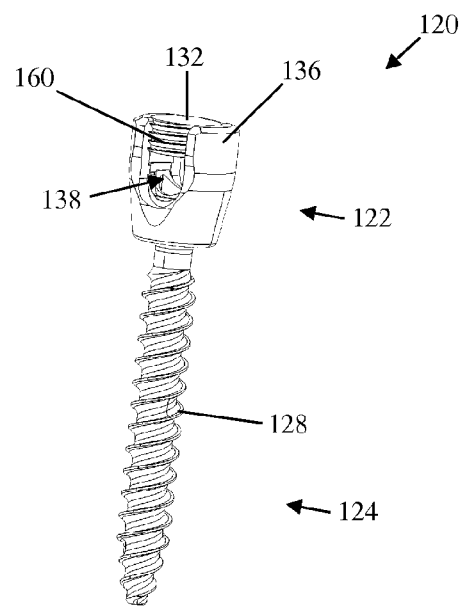
Fig. 15  Fig. 16
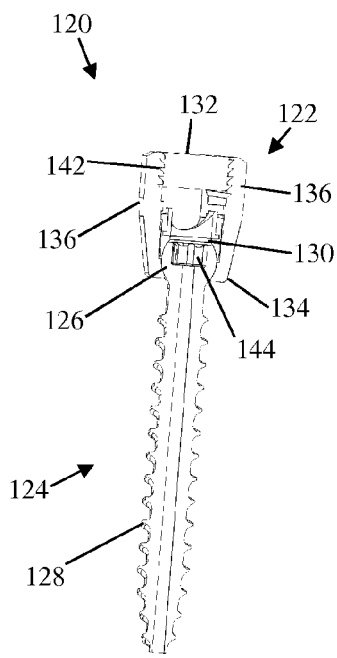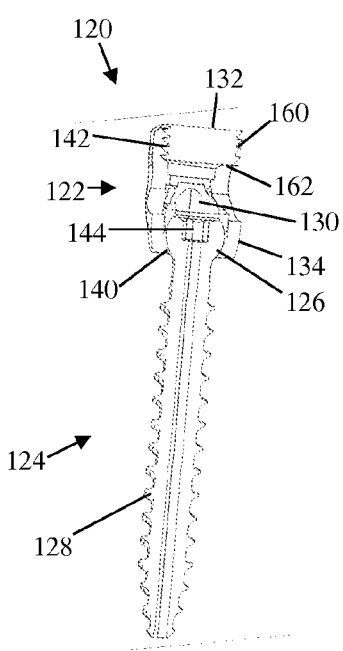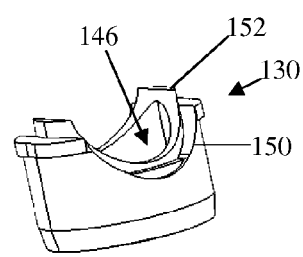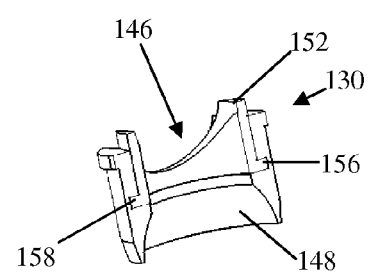
Fig. 17  Fig. 18  Fig. 19
Fig. 20

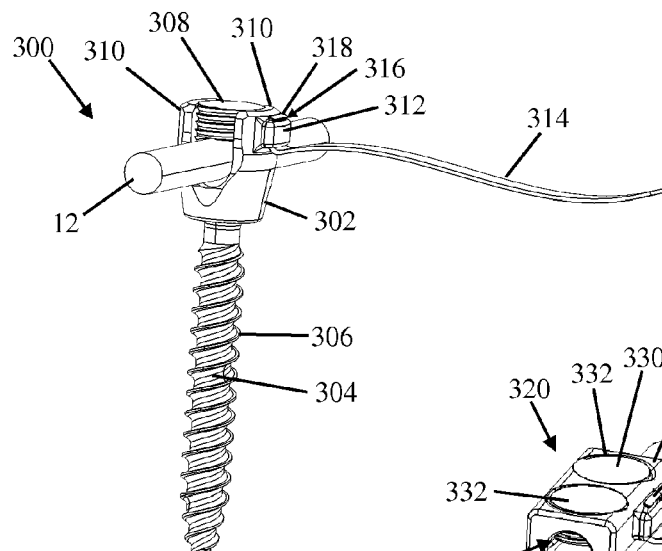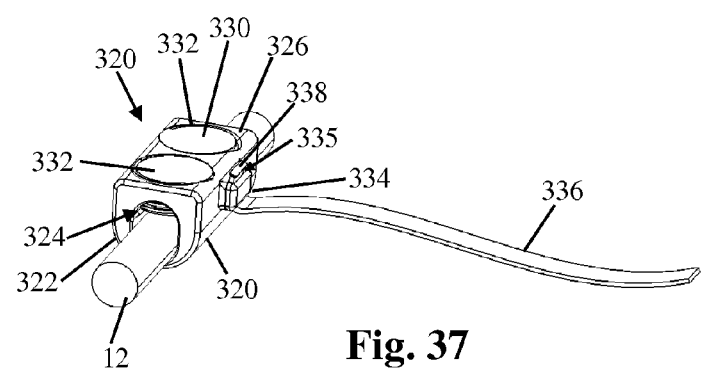
Fig. 36  Fig. 37
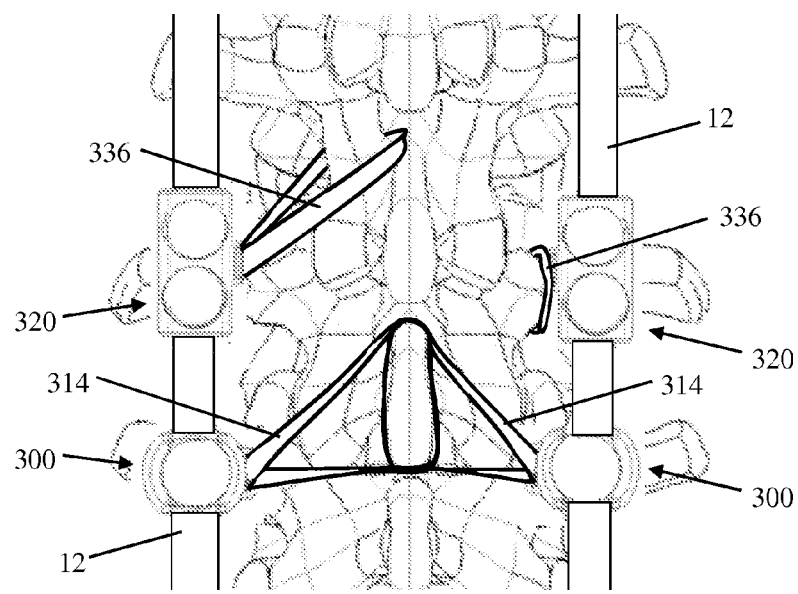
Fig. 38

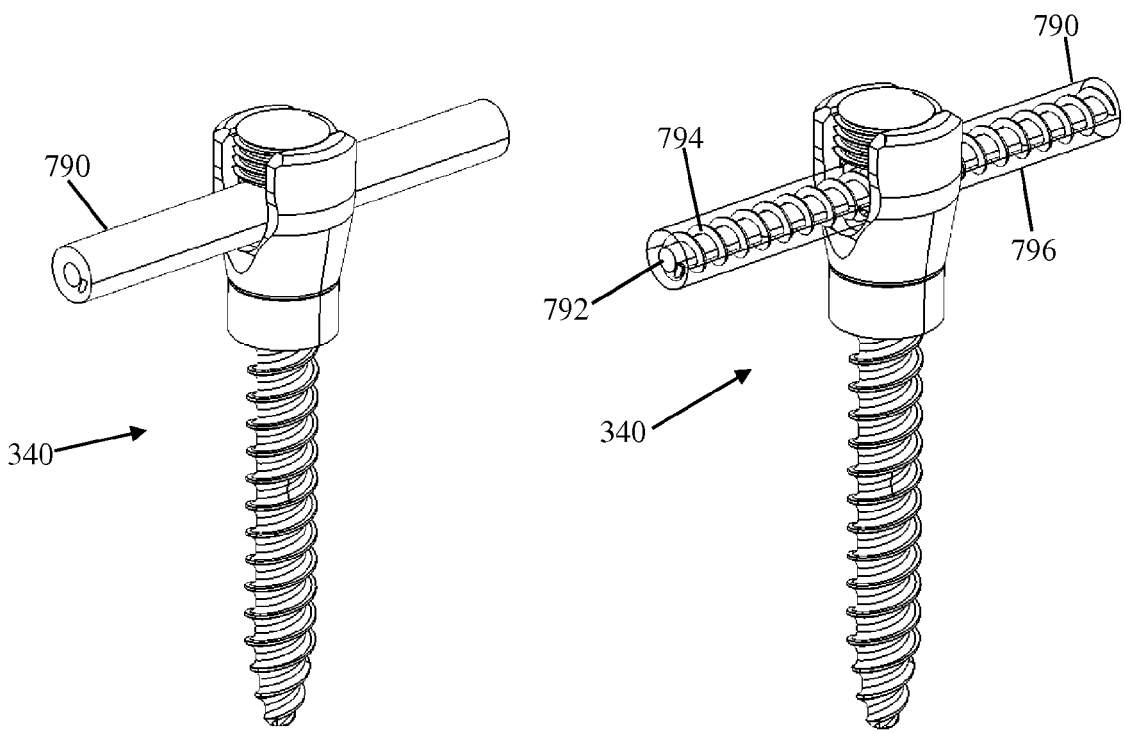
Fig. 42          Fig. 43
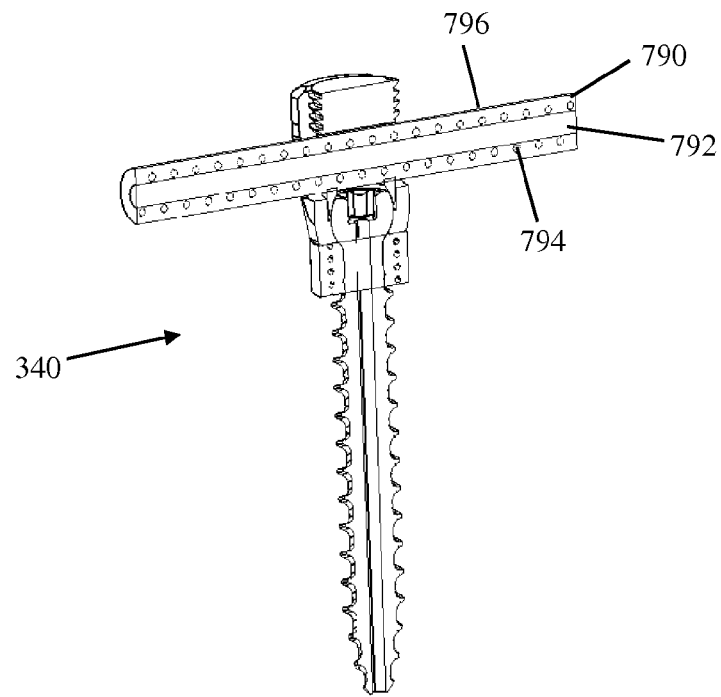
Fig. 44

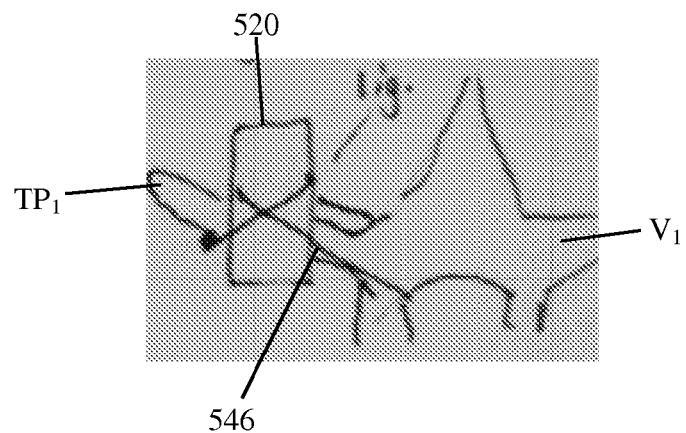
Fig. 65
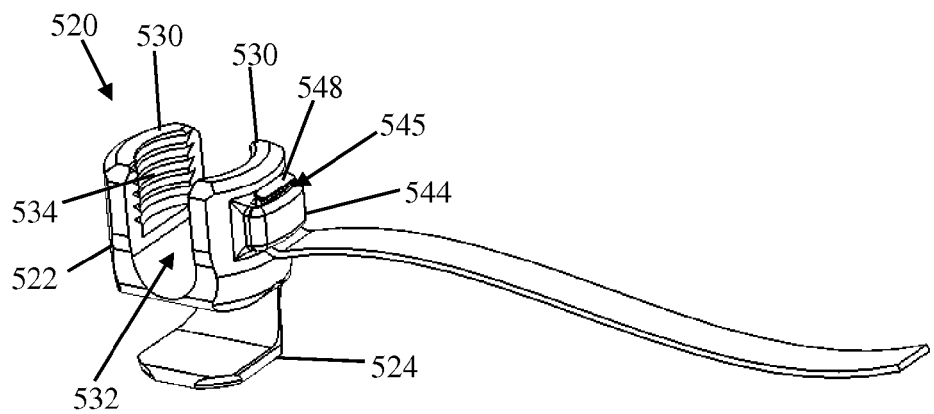
Fig. 66
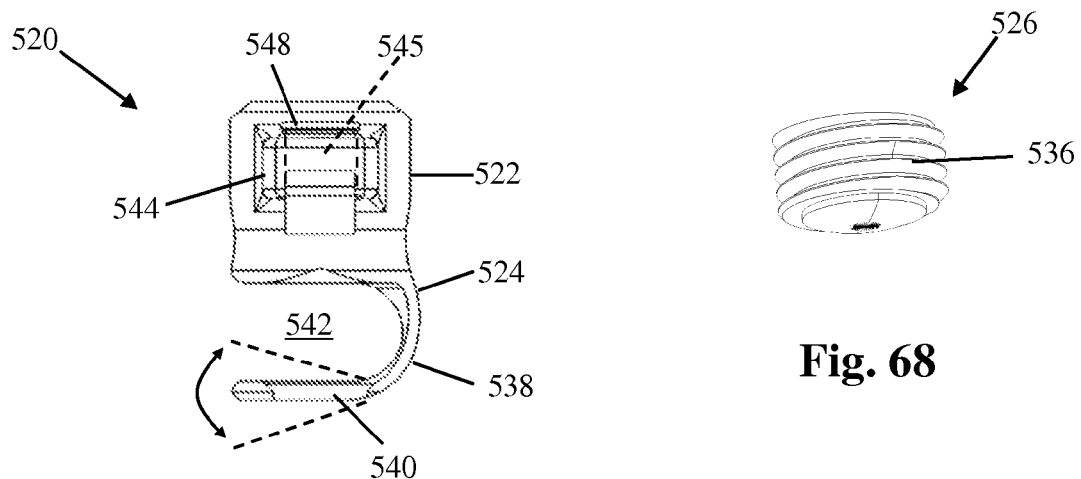
Fig. 67
Fig. 68

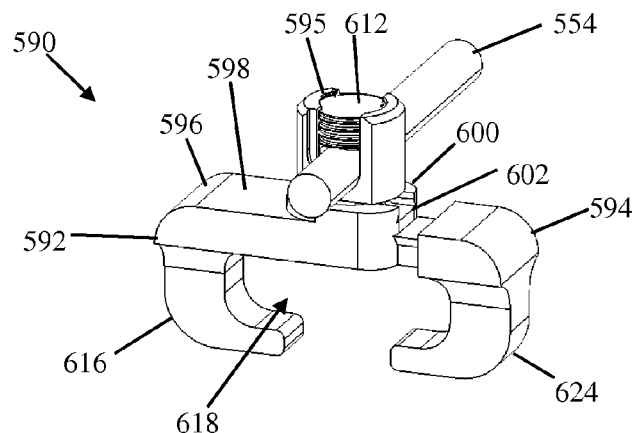
Fig. 73
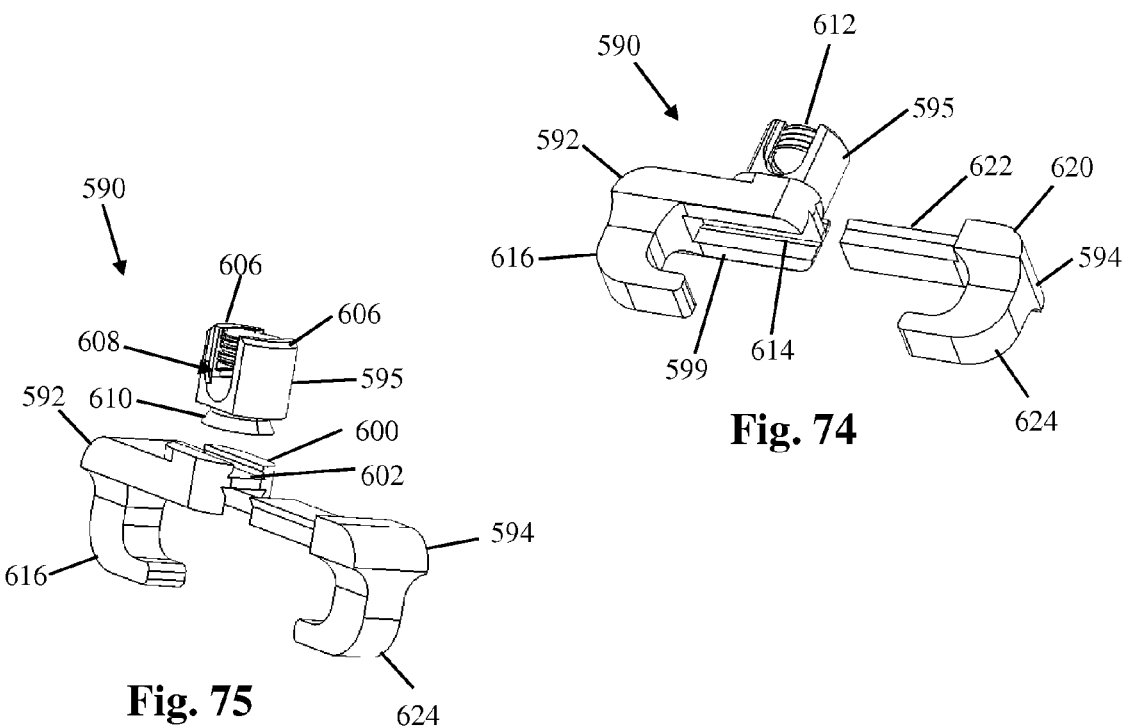
Fig. 74
Fig. 75
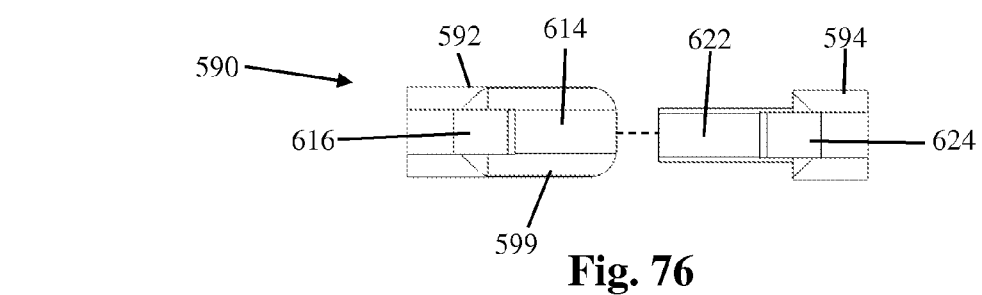
Fig. 76

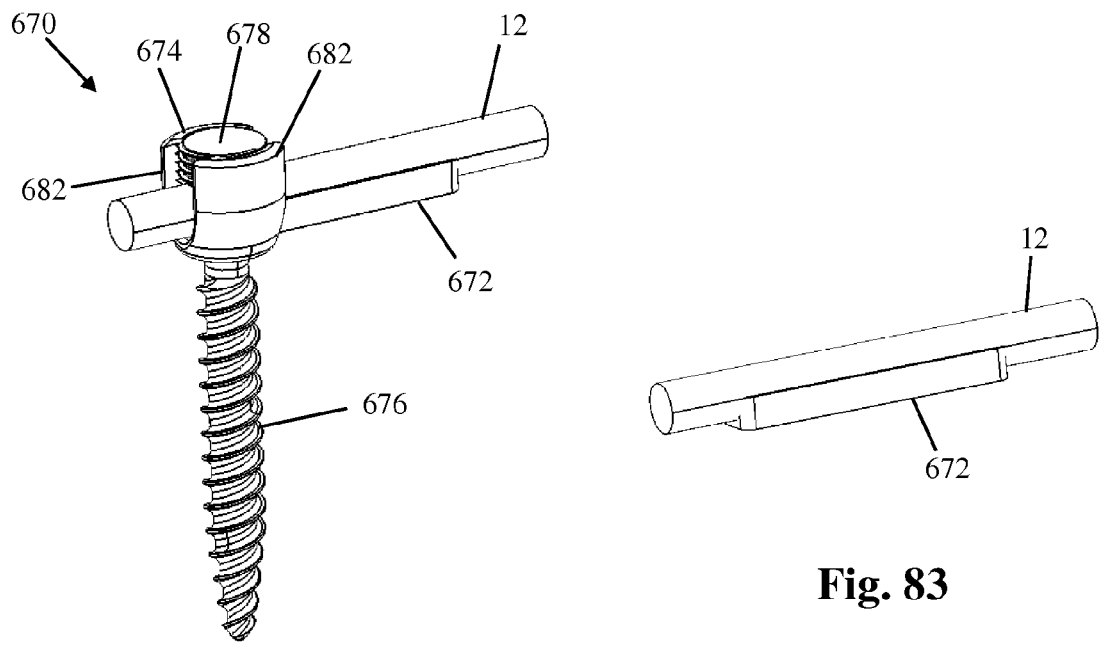
Fig. 82
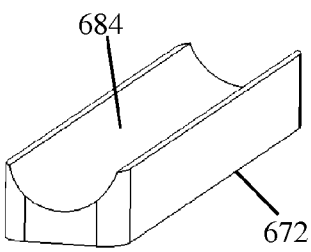
Fig. 83
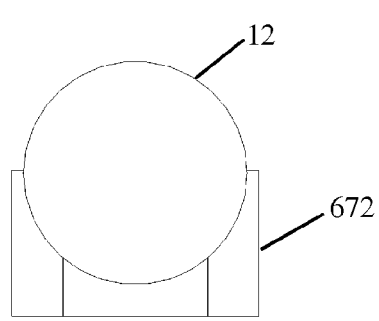
Fig. 84
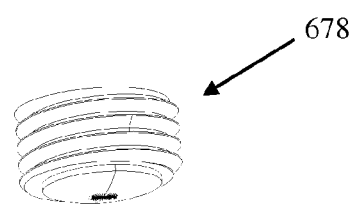
Fig. 85
Fig. 86

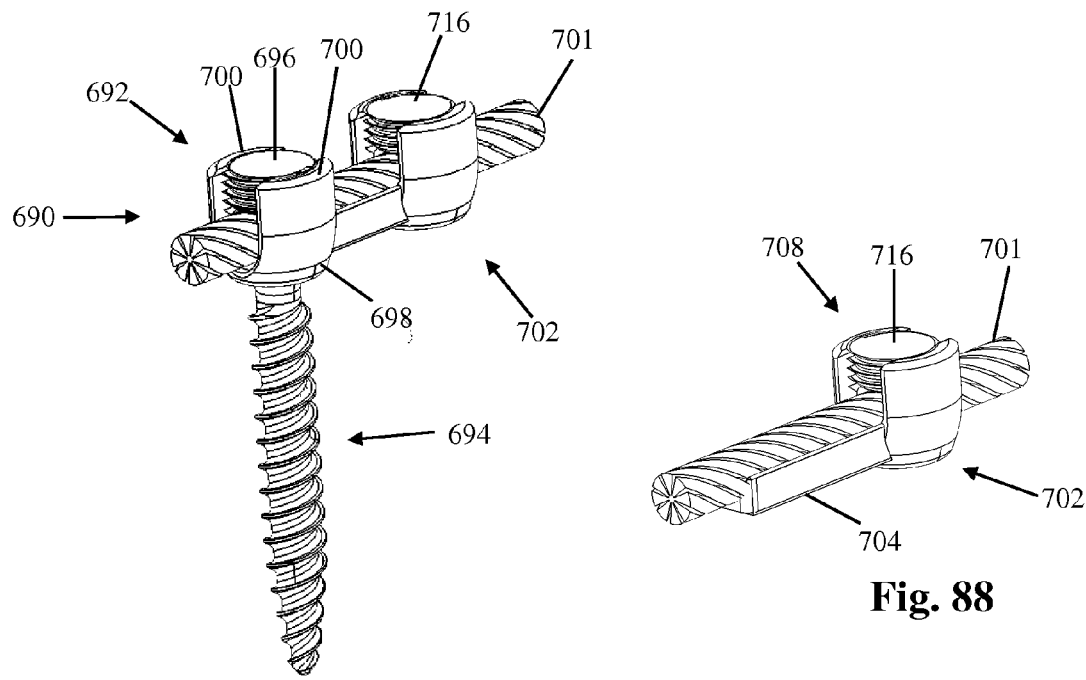
Fig. 87
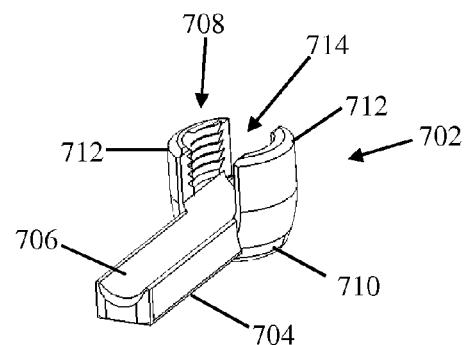
Fig. 88
Fig. 89
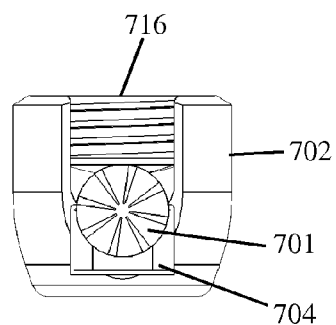
Fig. 90
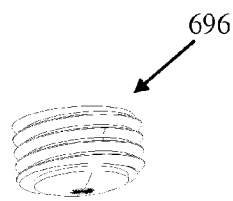
Fig. 91

SPINAL FIXATION CONSTRUCTS AND RELATED METHODS

CROSS-REFERENCE TO RELATED APPLICATIONS

This application is a non-provisional utility application which claims the benefit of priority under 35 U.S.C. § 119(e) to U.S. Provisional Application 61/988,066, filed on May 2, 2014, the entire contents of which are incorporated by reference into this disclosure as if set forth in its entirety herein.

FIELD

The present application relates generally to implants and methods used with, or forming part of, a spinal fixation construct and directed at preventing the occurrence of or reducing the degree of adjacent segment pathology and failures occurring at either the distal junction (DJK) or proximal junction (PJK).

BACKGROUND

The spine is formed of a column of vertebra that extends between the cranium and pelvis. The three major sections of the spine are known as the cervical, thoracic and lumbar regions. There are 7 cervical vertebrae (C1-C7), 12 thoracic vertebrae (T1-T12), and 5 lumbar vertebrae (L1-L5), with each of the 24 vertebrae being separated from each other by an intervertebral disc. A series of about 9 fused vertebrae extend from the lumbar region of the spine and make up the sacral and coccygeal regions of the vertebral column. The natural curvature of the spine includes a combination of lordosis and kyphosis. Specifically, the cervical and lumbar portions of the spine exhibit a natural lordotic curvature, meaning that they are set in a curve that is anteriorly convex (and posteriorly concave). The thoracic portion of the spine has a naturally kyphotic curvature, meaning that it is set in a curve that is anteriorly concave (and posteriorly convex).

The main functions of the spine are to provide skeletal support and protect the spinal cord. Even slight disruptions to either the intervertebral discs or vertebrae can result in serious discomfort as well as compression of nerve fibers either within the spinal cord or extending from the spinal cord. If a disruption to the spine becomes severe enough, severe pain, disability and damage to a nerve or part of the spinal cord may occur and can result in partial to total loss of bodily functions (e.g., walking, talking, breathing, etc.). Therefore, it is of great interest and concern to be able to both correct and prevent any ailments of the spine.

Fixation systems are often surgically implanted to stabilize or immobilize a portion of the spine. They are generally utilized during spinal fusion procedures to immobilize the applicable vertebrae until bone growth occurs to effect the fusion and/or to correct vertebral alignment issues. Fixation systems often use a combination of rods, plates, pedicle screws, and bone hooks to attach a fixation construct to the affected vertebrae. The configuration required for each procedure and patient varies due to the ailment being treated, the specific method of treatment (e.g. surgical approach, etc. . . . ) and the patient's specific anatomical characteristics.

Depending upon the pathology presented, correction of spinal ailments may involve only one vertebral level (i.e. a single intervertebral disc and the two vertebral bodies adjacent that intervertebral disc) or multiple spinal levels. An extreme example of a multiple level treatment relates to deformity correction (e.g. scoliosis correction) in which a screw and rod construct is implanted along a significant length of the spine in an attempt to forcibly correct or maintain a desired spinal alignment.

Whatever the treatment, the goal remains to improve the quality of life for the patient. In the vast majority of cases this goal is achieved, however in some instances patients who receive implants to treat the primary pathology develop a secondary condition called junctional disease. Most commonly this occurs at the proximal or cephalad area of spinal instrumentation and is then termed adjacent segment pathology. Clinical Adjacent Segment Pathology (CASP) refers to clinical symptoms and signs related to adjacent segment pathology. Radiographic Adjacent Segment Pathology (RASP) refers to radiographic changes that occur at the adjacent segment. A subcategory of CASP and RASP that occurs at the proximal end of the instrumentation is termed proximal junctional kyphosis (PJK). PJK may be defined in several manners and commonly is specified as kyphosis measured from one segment cephalad to the upper end instrumented vertebra to the proximal instrumented vertebra with abnormal value defined as 10 degrees or greater. In practice this often means that the patient's head and/or shoulders tend to fall forward to a greater degree than should normally occur. Sometimes the degree is significant.

Adjacent segment pathology can occur as either a degenerative, traumatic or catastrophic condition and sometimes as a result from a combination of factors. Degenerative conditions are ones that occur over a period of time, normally 5 or 6 years but can occur at an accelerated rate particularly with altered mechanics related to spinal fusion. As a result the patient's head and/or shoulder region(s) fall forward gradually over time. Traumatic and catastrophic conditions occur as a generally sudden shifting of the vertebral body immediately cephalad to the upper end instrumented vertebra and can lead to sudden changes in spinal alignment with marked symptoms noted by the patient.

Whether the condition is degenerative, traumatic or catastrophic, the exact cause of adjacent segment pathology is uncertain. Generally, it is believed that adjacent segment pathology and more specifically PJK is a result of excess strain and stress on the proximal instrumented spinal segment which is then at least partially transferred to the bone structures, disc, ligaments and other soft tissues, causing a loss of normal structural integrity and mechanical properties. The resultant effect can be a forward (i.e. kyphotic) shift of the adjacent non-instrumented vertebral body. One such theory is that this strain and stress is caused by suboptimal alignment and/or balance of the screw and rod construct. Another theory is that the rigidity of the screw and rod construct causes the problem in that the transition from a motion-restrained segment to a motion-unrestrained segment is too much for the non-instrumented (unrestrained) segment to handle over time. Yet another theory speculates that the specific level at which the proximal instrumented vertebra is located is of vital importance in that some levels may be better suited to handle a proximal termination of a fixation construct than others.

Thus there remains a need for continued improvements and new systems for spinal fixation with a specific goal of preventing the occurrence of or reducing the degree of adjacent segment pathology and failures occurring at either the distal junction (DJK) or proximal junction (PJK). The implants and techniques described herein are directed towards overcoming these challenges and others associated with posterior spinal fixation.

BRIEF DESCRIPTIONS OF THE DRAWINGS

Many advantages of the present invention will be apparent to those skilled in the art with a reading of this specification in conjunction with the attached drawings, wherein like reference numerals are applied to like elements and wherein:

FIGS. 15 and 16 are perspective views of one example of a polyaxial bone anchor forming part of the vertebral fixation system of FIG. 1;

FIGS. 17 and 18 are perspective sectional views of the bone anchor of FIG. 15;

FIGS. 19 and 20 are perspective and sectional views, respectively, of a rod seat insert forming part of the bone anchor of FIG. 15;

FIG. 36 is a perspective view of an example of a bone anchor with attached tether configured for use with and forming part of the vertebral fixation system of FIG. 1;

FIG. 37 is a perspective view of an example of a rod attachment with attached tether configured for use with and forming part of the vertebral fixation system of FIG. 1;

FIG. 38 is a plan view of the bone anchor of FIG. 36 and the rod attachment of FIG. 37 in use on a human spine;

FIGS. 42 and 43 are perspective view, respectively, of the bone anchor of FIG. 39 in use with an example of a flexible rod suitable for use with the vertebral fixation system of FIG. 1;

FIG. 44 is a sectional view of the bone anchor and flexible rod combination of FIG. 42;

FIG. 65 is a plan view of a partial spine with another example of a bone anchor suitable for use with the vertebral fixation system of FIG. 1 attached thereto;

FIG. 66 is a perspective view of the bone anchor of FIG. 65;

FIG. 67 is a side plan view of the bone anchor of FIG. 65;

FIG. 68 is a perspective view of a locking element forming part of the bone anchor of FIG. 65;

FIGS. 73-75 are perspective views of an alternative example of a rib clamp forming part of the bone anchor of FIG. 72;

FIG. 76 is an exploded plan view of the rib clamp of FIG. 73;

FIG. 82 is a perspective view of an example of a bone anchor having a rod bumper configured for use with the spinal fixation system of FIG. 1;

FIGS. 83 and 84 are perspective and plan views, respectively, of the spinal rod and rod bumper of FIG. 82;

FIG. 85 is a perspective view of the rod bumper of FIG. 82;

FIG. 86 is a perspective view of a locking element forming part of the bone anchor of FIG. 82;

FIG. 87 is a perspective view of an alternative example of a bone anchor and rod bumper combination configured for use with the spinal fixation system of FIG. 1;

FIGS. 88 and 89 are perspective and plan views, respectively, of the spinal rod and rod bumper of FIG. 87;

FIG. 90 is a perspective view of the rod bumper of FIG. 87;

FIG. 91 is a perspective view of a locking element forming part of the bone anchor of FIG. 87;

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The vertebral fixation system and methods described herein boast a variety of inventive features and components that warrant patent protection, both individually and in combination.

This disclosure describes a variety of transitional or terminal components that may be implanted as part of a spinal fixation construct to decrease the potential for subsequent development of junctional disease or failure. In the examples shown only the cephalad most level (for terminal hardware) or levels (for multilevel transitional hardware) of the fixation construct (e.g. those utilizing the exemplary components described herein) are illustrated. It should be appreciated, however, that the entire fixation construct may extend any number of levels from a single level construct to a long construct spanning multiple spinal levels and multiple spinal regions from the lumbosacral to cervical regions (such as the example construct illustrated in FIG. 1), and with any variety of combinations of known anchors, rods, and connectors. It should also be appreciated that the exemplary terminal and/or transitional components may additionally or alternatively be utilized at the caudal end of the fixation construct. Moreover, although the vertebral fixation systems described herein may be used along any aspect of the spine (e.g. anterior, posterior, antero-lateral, postero-lateral) they are particularly suited for implantation along a posterior aspect of the spine.

Figure 1:
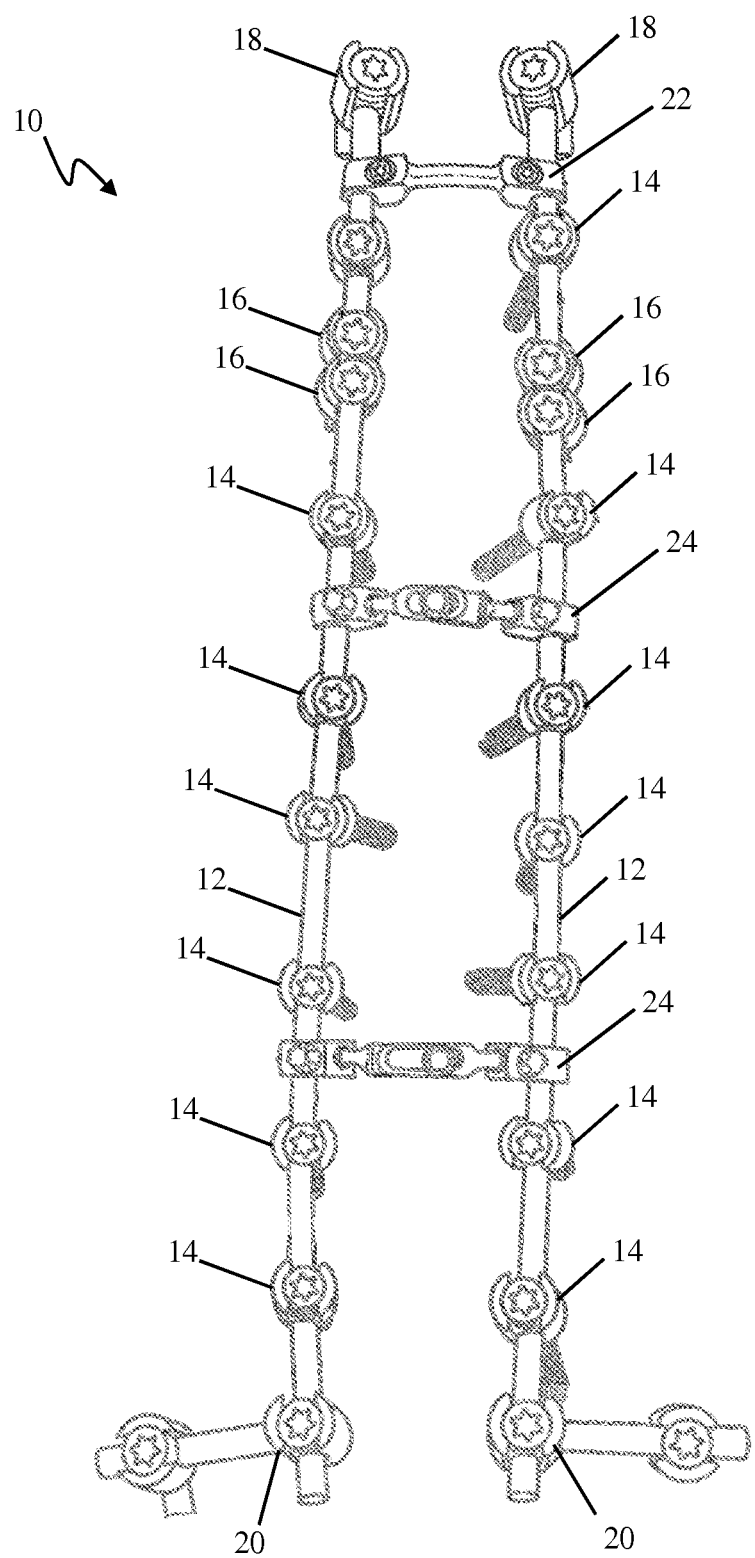
FIG. 1 is a perspective view of one example of a vertebral fixation system including various elements described in this disclosure.
Figure 2:
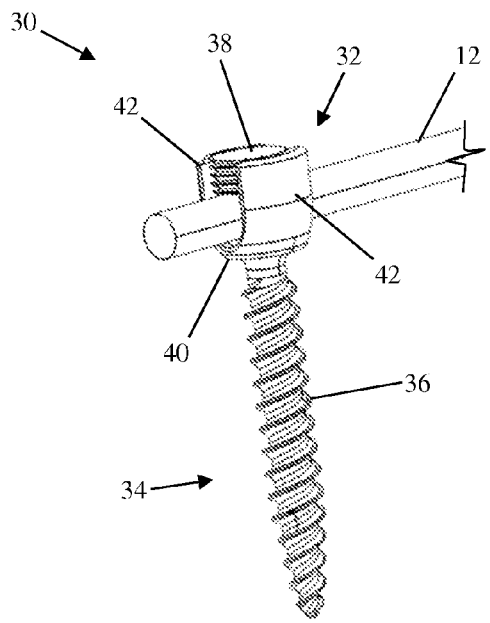
FIGS. 2 and 3 are perspective views of one example of a fixed angle bone anchor forming part of the vertebral fixation system of FIG. 1.
Figure 3:
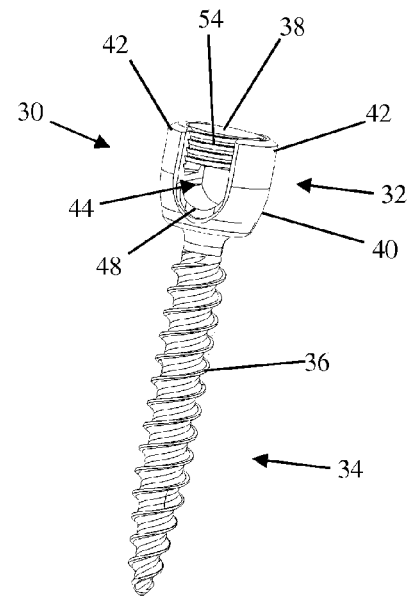
Figure 4:
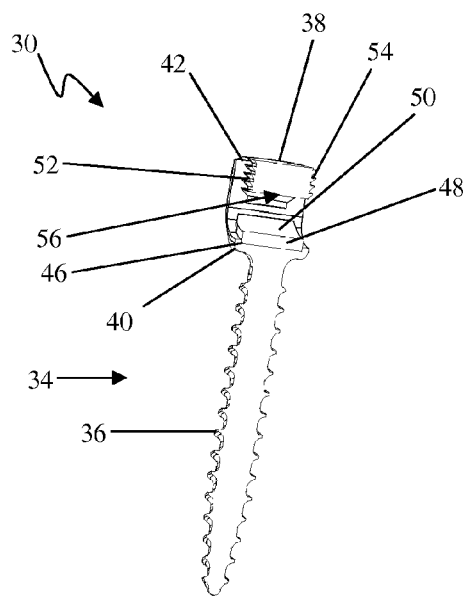
FIGS. 4 and 5 are perspective sectional views of the bone anchor of FIG. 2.
Figure 5:
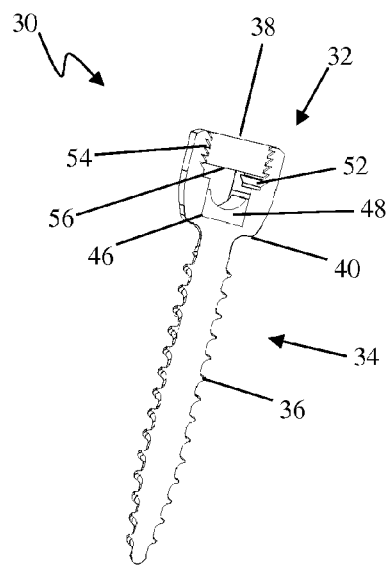

FIG. 1 illustrates an example of a vertebral fixation system 10 of the type that is used with the devices and methods described in this disclosure. By way of example, the vertebral fixation system 10 is a screw-and-rod construct adapted for implantation along the posterior aspect of the human spinal column. The vertebral fixation system 10 includes a pair of elongate rods 12 dimensioned to span multiple vertebral levels, a plurality of threaded bone anchors 14, a plurality of hook-type bone anchors 16, and a plurality of transverse connectors 22, 24 dimensioned to rigidly engage each of the elongate rods 12 so as to hold each rod in place relative to the other. The transverse connectors 22, 24 may be provided as fixed connectors 22 or adjustable connectors 24, in any quantity that is required by the surgeon performing the implantation surgery. Proximal bone anchors 18 are provided at the proximal (cephalad) terminus of the assembly. Distal bone anchors 20 are provided at the distal (caudal) terminus of the assembly. It is contemplated that any of the examples of bone anchors and other transition assemblies described herein may be substituted for the proximal bone anchors 18 and/or distal bone anchors 20 which are traditionally rigid and identical to the other bone anchors used throughout the construct. It is also contemplated that the examples of flexible transition segments described herein may replace existing hardware at the proximal and/or distal terminus of the vertebral fixation system 10 such that there is no additional surgical footprint realized. It is further contemplated that the examples of flexible transition segments described herein may augment existing hardware at the proximal and/or distal terminus of the vertebral fixation system 10 such that there is additional added surgical footprint realized. This may be more applicable with the various embodiments to that can be installed with minimal disruption of additional muscle tissue and/or ligament structure. Finally, as previously noted junctional disease or failure can be a problem at either the proximal terminus or the distal terminus (or both) of vertebral fixation systems. Therefore, although the various examples disclosed herein may be described in terms of proximal terminus and proximal joint disease (for ease of disclosure) it is to be understood that any of the example embodiments are also applicable and may be used at the distal terminus of the vertebral fixation system without deviating from the scope of this disclosure.

FIGS. 2-5 illustrate a first example of a bone anchor configured for use with the vertebral fixation system 10 described above. By way of example, the bone anchor 30 is a fixed angle screw having a housing 32 for capturing and locking therein a spinal rod 12, a shank 34 including a thread feature 36 suitable for stable fixation to vertebral bone, and a locking element 38 configured for locking the spinal rod 12 within the housing 32.

The housing 32 has a base 40 that mates (or is integrally formed) with the shank 34 and a pair of upstanding arms 42 separated by and partially defining a rod channel 44 sized and configured to receive the spinal rod 12 therein. The base includes a recess 46 formed within the rod channel and configured to receive a rod seat 48. The rod seat 48 is a block of material sized and dimensioned to snugly fit within the recess 46 and having a concave surface 50 that forms the lower portion of the rod channel 44. The concave surface 50 is configured to engage the generally cylindrical spinal rod 12 and provide a seat for the spinal rod 12. Significantly, the rod seat 48 of the instant example may be formed of a semi-rigid elastomeric material that allows for some movement (e.g. vertical shifting, axial rotation, pivoting, and/or translation) of the spinal rod 12 within the housing 32 while maintaining a frictional association with the spinal rod 12 (and thus preventing unrestricted movement of the rod). The upstanding arms 42 include a locking element engagement feature 52 disposed on the interior face of each arm 42. The locking element engagement feature 52 mates with a complementary housing engagement feature 54 on the locking element 38, described in further detail below.

The locking element 38 is attachable to the housing 32 after the spinal rod 12 has been seated within the rod channel 44. In the example presently described, the locking element 38 comprises a setscrew having a housing engagement feature 54 and a rod engagement surface 56. The housing engagement feature 54 complementarily engages the locking element engagement feature 46 of the upstanding arms 42. The rod engagement surface 56 is configured to engage the spinal rod 12 and may be planar, convex, or concave. By way of example, the locking element 38 is made of a rigid material (e.g. titanium).

In use, after the spinal rod 12 has been seated within the rod channel 44, the locking element 38 is inserted between the upstanding arms 42 such that the housing engagement feature 54 on the locking element 38 engages the locking element engagement features 46 on each of the upstanding arms 42. The locking element 38 is then advanced via rotation to exert a force on the spinal rod 12 and frictionally lock the spinal rod 12 within the housing 32 (and between the locking element 38 and the rod seat 48). After implantation, the semi-rigid nature of the elastomeric rod seat 48 will allow the construct to absorb some force and experience some potential alignment correction that may occur from natural shifting of the patient's body, thereby potentially alleviating some conditions that may lead to junctional disease or failure (e.g. PJK, DJK, etc.).

In the instant example (and others described below), the housing 32 and shank 34 are provided in a fixed relationship so that no relative movement is possible between them. This may be achieved by way of example through secure mating of separate parts or by a single part having an integral housing 32 and shank. Alternatively, the housing 32 and shank 34 may be mated with a polyaxial engagement such that the housing 32 can pivot relative to the shank 34 in any direction. The engagement may also be such that the pivoting movement may be inhibited in one or more directions. By way of example, the housing 32 and shank 34 may be mated with a uniplanar engagement such that the housing 32 pivots relative to the shank 32 in a single plane. Many of these alternative examples are described in further detail below.

Figure 6:
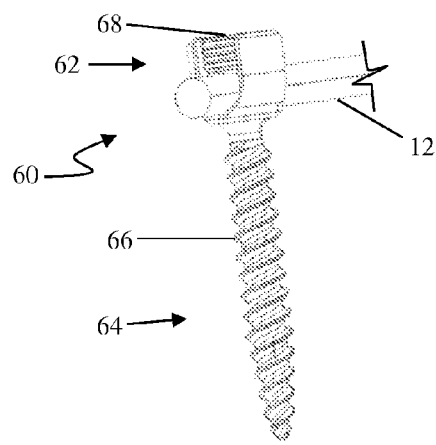
FIGS. 6 and 7 are perspective views of another example of a fixed angle bone anchor forming part of the vertebral fixation system of FIG. 1.
Figure 7:
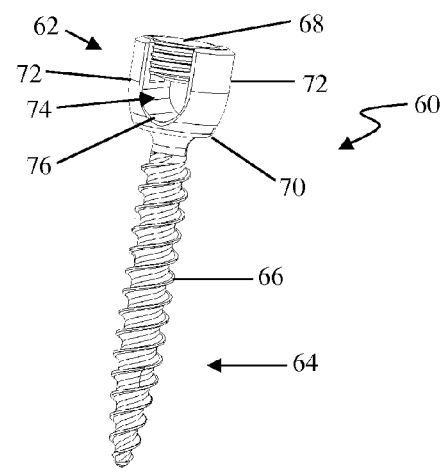
Figure 8:
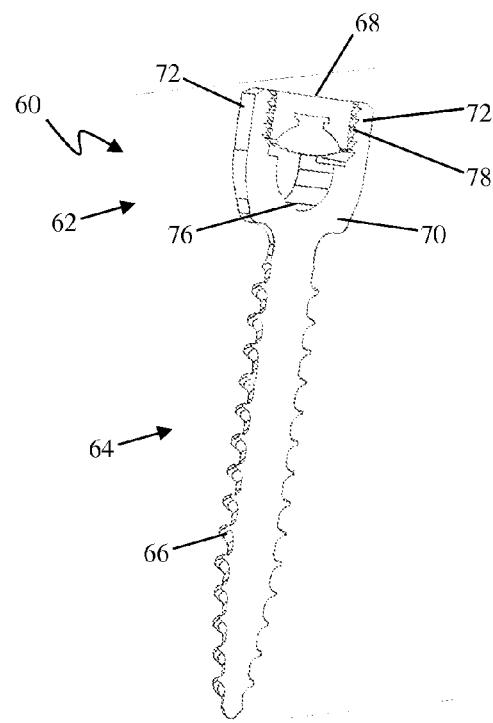
FIG. 8 is a perspective sectional view of the bone anchor of FIG. 6.

FIGS. 6-8 illustrate another example of a bone anchor configured for use with the vertebral fixation system 10 described above. By way of example, the bone anchor 60 is a fixed angle screw having a housing 62 for capturing and locking therein a spinal rod 12, a shank 64 including a thread feature 66 suitable for stable fixation to vertebral bone, and a locking element 68 configured for locking the spinal rod 12 within the housing 62.

The housing 62 has a base 70 that mates (or is integrally formed) with the shank 64 and a pair of upstanding arms 72 separated by and partially defining a rod channel 74 sized and configured to receive the spinal rod 12 therein. The base includes a rod seat 76 comprising an upward-facing concave surface that forms the lower portion of the rod channel 74. The rod seat 76 is configured to engage the generally cylindrical spinal rod 12 and provide a seat for the spinal rod 12. In the instant example, the rod seat 76 is composed of the same rigid material as the bone anchor 60 (e.g. titanium). The upstanding arms 72 include a locking element engagement feature 78 disposed on the interior face of each arm 72. The locking element engagement feature 78 mates with a complementary housing engagement feature 80 on the locking element 68, described in further detail below.

Figure 9:
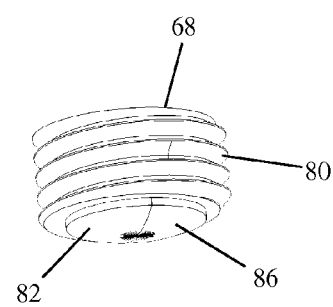
FIGS. 9 and 10 are perspective and sectional views, respectively, of a locking element forming part of the bone anchor of FIG. 6.
Figure 10:
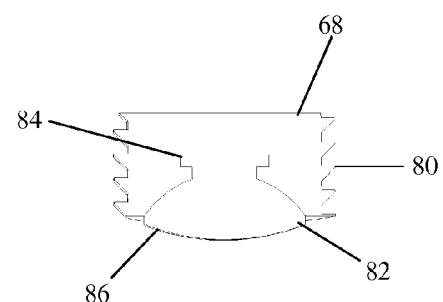
Figure 11:
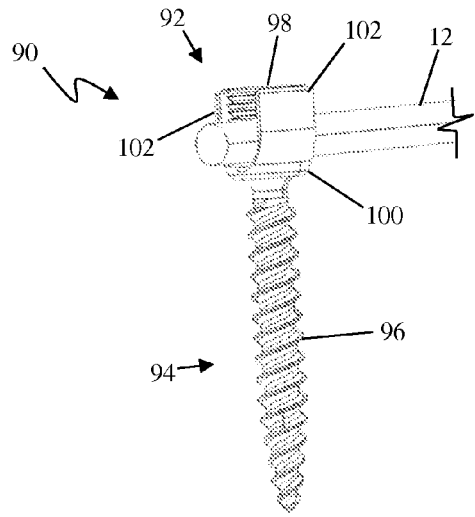
FIGS. 11 and 12 are perspective views of still another example of a fixed angle bone anchor forming part of the vertebral fixation system of FIG. 1.
Figure 12:
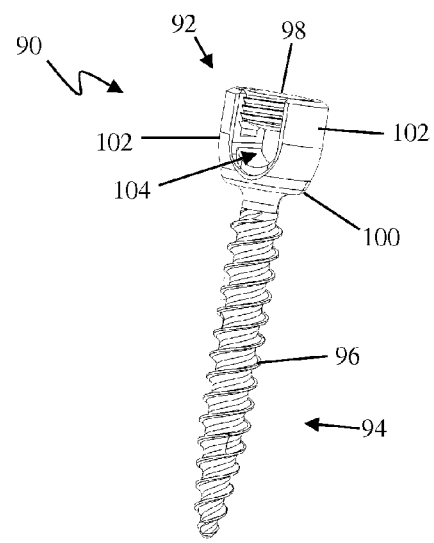
Figure 13:
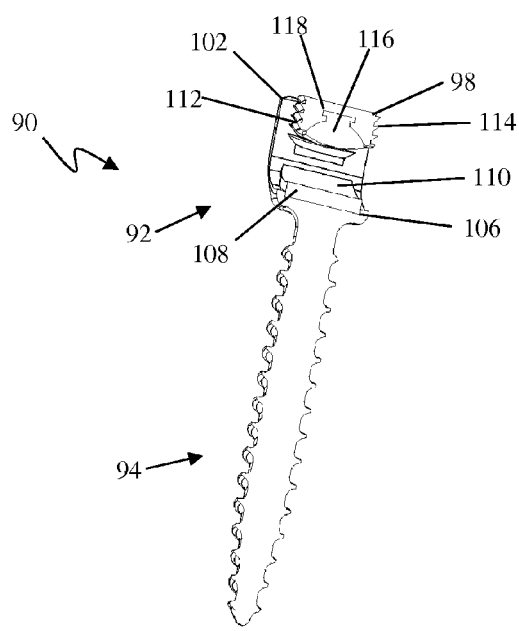
FIGS. 13 and 14 are perspective sectional views of the bone anchor of FIG. 11.
Figure 14:
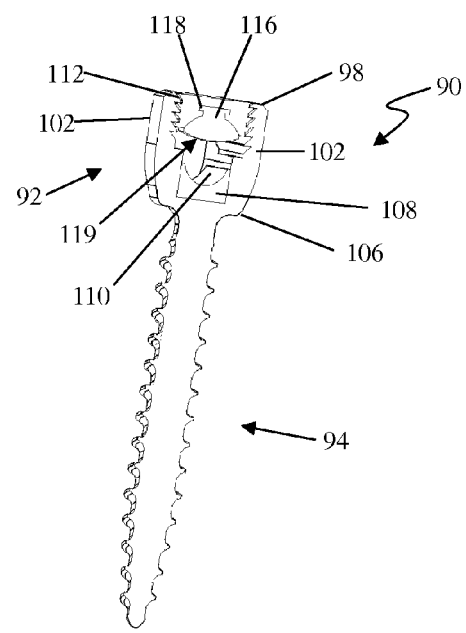

FIGS. 9 and 10 illustrate the locking element 68 in greater detail. The locking element 68 is attachable to the housing 62 after the spinal rod 12 has been seated within the rod channel 64. In the example presently described, the locking element 68 comprises a set screw having a housing engagement feature 80 and a rod engagement insert 82. The housing engagement feature 80 complementarily engages the locking element engagement feature 78 of the upstanding arms 72. The rod engagement insert 82 is a block of material sized and dimensioned to snugly fit within a recess 84 formed within the locking element 68 and having a convex surface 86 that forms the upper boundary of the rod channel 74 when the locking element 68 is mated with the housing 62. The convex surface 86 is configured to engage the generally cylindrical spinal rod 12 and exert a force on the spinal rod 12 to enable the frictional lock. By way of example, the locking element 38 is made of a rigid material (e.g. titanium). Significantly, the rod engagement insert 82 of the instant example may be formed of a semi-rigid elastomeric material that allows for some movement (e.g. vertical shifting, axial rotation, pivoting, and/or translation) of the spinal rod 12 within the housing 62 while maintaining a frictional association with the spinal rod 12 (and thus preventing unrestricted movement of the rod). The rod engagement insert 82 is secured within the recess 84 via a physical barrier (i.e. flange and lip interaction) however other methods of securing the rod engagement insert 82 within the recess 84 are possible.

In use, after the spinal rod 12 has been seated within the rod channel 74, the locking element 68 is inserted between the upstanding arms 72 such that the housing engagement feature 80 on the locking element 68 engages the locking element engagement features 78 on each of the upstanding arms 72. The locking element 68 is then advanced via rotation to exert a force on the spinal rod 12 and frictionally lock the spinal rod 12 within the housing 62 (and between the locking element 68 and the rod seat 76). After implantation, the semi-rigid nature of the elastomeric rod engagement insert 82 will allow the construct to absorb some force and experience some potential alignment correction that may occur from natural shifting of the patient's body, thereby potentially alleviating some conditions that may lead to junctional disease or failure (e.g. PJK, DJK, etc.).

FIGS. 11-14 illustrate another example of a bone anchor configured for use with the vertebral fixation system 10 described above. By way of example, the bone anchor 90 is a fixed angle screw having a housing 92 for capturing and locking therein a spinal rod 12, a shank 96 including a thread feature 96 suitable for stable fixation to vertebral bone, and a locking element 98 configured for locking the spinal rod 12 within the housing 92.

The housing 92 has a base 100 that mates (or is integrally formed) with the shank 94 and a pair of upstanding arms 102 separated by and partially defining a rod channel 104 sized and configured to receive the spinal rod 12 therein. The base includes a recess 106 formed within the rod channel and configured to receive a rod seat 108. The rod seat 108 is a block of material sized and dimensioned to snugly fit within the recess 106 and having a concave surface 110 that forms the lower portion of the rod channel 104. The concave surface 110 is configured to engage the generally cylindrical spinal rod 12 and provide a seat for the spinal rod 12. Significantly, the rod seat 108 of the instant example may be formed of a semi-rigid elastomeric material that allows for some movement (e.g. vertical shifting, axial rotation, pivoting, and/or translation) of the spinal rod 12 within the housing 92 while maintaining a frictional association with the spinal rod 12 (and thus preventing unrestricted movement of the rod). The upstanding arms 102 include a locking element engagement feature 112 disposed on the interior face of each arm 102. The locking element engagement feature 112 mates with a complementary housing engagement feature 114 on the locking element 98, described in further detail below.

The locking element 98 is attachable to the housing 92 after the spinal rod 12 has been seated within the rod channel 104. In the example presently described, the locking element 98 comprises a setscrew having a housing engagement feature 114 and a rod engagement insert 116. The housing engagement feature 114 complementarily engages the locking element engagement feature 112 of the upstanding arms 102. The rod engagement insert 116 is a block of material sized and dimensioned to snugly fit within a recess 118 formed within the locking element 98 and having a convex surface 119 that forms the upper boundary of the rod channel 104 when the locking element 98 is mated with the housing 92. The convex surface 119 is configured to engage the generally cylindrical spinal rod 12 and exert a force on the spinal rod 12 to enable the frictional lock. By way of example, the locking element 98 is made of a rigid material (e.g. titanium). Significantly, the rod engagement insert 116 of the instant example may be formed of a semi-rigid elastomeric material that allows for some movement (e.g. vertical shifting, axial rotation, pivoting, and/or translation) of the spinal rod 12 within the housing 92 while maintaining a frictional association with the spinal rod 12 (and thus preventing unrestricted movement of the rod). The rod engagement insert 116 is secured within the recess 118 via a physical barrier (i.e. flange and lip interaction) however other methods of securing the rod engagement insert 116 within the recess 118 are possible.

In use, after the spinal rod 12 has been seated within the rod channel 104, the locking element 98 is inserted between the upstanding arms 102 such that the housing engagement feature 114 on the locking element 98 engages the locking element engagement features 112 on each of the upstanding arms 102. The locking element 98 is then advanced via rotation to exert a force on the spinal rod 12 and frictionally lock the spinal rod 12 within the housing 92 (and between the locking element 98 and the rod seat 108). After implantation, the semi-rigid nature of both the elastomeric rod seat 108 and the rod engagement insert 116 will allow the construct to absorb some force and experience some potential alignment correction that may occur from natural shifting of the patient's body, thereby potentially alleviating some conditions that may lead to junctional disease or failure (e.g. PJK, DJK, etc.).

FIGS. 15-20 illustrate another example of a bone anchor configured for use with the vertebral fixation system 10 described above. By way of example, the bone anchor 120 is a polyaxial screw having a housing 122 for capturing and locking therein a spinal rod 12, a shank 124 including a generally spherical head 126 and a thread feature 128 suitable for stable fixation to vertebral bone, a seat member 130, and a locking element 132 configured for locking the spinal rod 12 within the housing 122.

The housing 122 has a base 134 that mates with the shank 124 and a pair of upstanding arms 136 separated by and partially defining a rod channel 138 sized and configured to receive the spinal rod 12 therein. The base 134 includes a recess 140 having a concave surface sized and dimensioned to receive the spherical head 126 of the shank 124. The spherical head 126 is able to rotate and pivot within the recess 140 such that the shank 124 may be disposed at any number of a plurality of angles relative to the housing 122. The upstanding arms 136 include a locking element engagement feature 142 disposed on the interior face of each arm 136. The locking element engagement feature 142 mates with a complementary housing engagement feature 160 on the locking element 132, described in further detail below.

The shank 124 further includes a driver recess 144 positioned at the top of the head 126 such that the driver recess 144 is accessible from the rod channel 138 prior to insertion of the locking element 132. The driver recess 144 is configured to engage a driver instrument (not shown) to enable implantation of the bone anchor 120 into a vertebral bone.

Referring to FIGS. 19 and 20, the seat member 130 is generally cylindrical in shape and has a lumen 146 extending longitudinally therethrough to allow passage of a driver instrument so that the driver instrument may engage the driver recess 144 of the shank 124. The lower portion of the lumen 146 has a concave surface 148 configured to receive and engage at least a portion of the generally spherical head 126 of the shank 124. The seat member 130 also includes a pair of opposing concave recesses 150 on the upper portion of the seat member 130. When properly assembled, the concave recesses 150 are aligned with and form part of the rod channel 138 for receiving the spinal rod 12.

The seat member 130 further includes a rod seat 152 disposed within the upper portion of the lumen 146. The rod seat 152 is a block of material sized and dimensioned to snugly fit within the lumen 146 and having a pair of concave surfaces 154 that form part of the lower portion of the rod channel 138. The concave surfaces 154 are configured to engage the generally cylindrical spinal rod 12 and provide a seat for the spinal rod 12. Significantly, the rod seat 152 of the instant example may be formed of a semi-rigid elastomeric material that allows for some movement (e.g. vertical shifting, axial rotation, pivoting, and/or translation) of the spinal rod 12 within the housing 122 while maintaining a frictional association with the spinal rod 12 (and thus preventing unrestricted movement of the rod). By way of example, the rod seat 152 is secured within the lumen 146 via a physical barrier interaction (i.e. a flange 156 on the rod seat 152 that is received within a recess 158 disposed within the lumen 146).

The locking element 132 is attachable to the housing 122 after the spinal rod 12 has been seated within the rod channel 138. In the example presently described, the locking element 132 comprises a setscrew having a housing engagement feature 160 and a rod engagement surface 162. The housing engagement feature 160 complementarily engages the locking element engagement feature 142 of the upstanding arms 136. The rod engagement surface 162 is configured to engage the spinal rod 12 and may be planar, convex, or concave. By way of example, the locking element 38 is made of a rigid material (e.g. titanium).

In use, after the spinal rod 12 has been seated within the rod channel 138, the locking element 132 is inserted between the upstanding arms 136 such that the housing engagement feature 160 on the locking element 132 engages the locking element engagement features 142 on each of the upstanding arms 136. The locking element 132 is then advanced via rotation to exert a force on the spinal rod 12 and frictionally lock the spinal rod 12 within the housing 122 (and between the locking element 132 and the rod seat 152). After implantation, the semi-rigid nature of the elastomeric rod seat 152 will allow the construct to absorb some force and experience some potential alignment correction that may occur from natural shifting of the patient's body, thereby potentially alleviating some conditions that may lead to junctional disease or failure (e.g. PJK, DJK, etc.).

Figure 21:
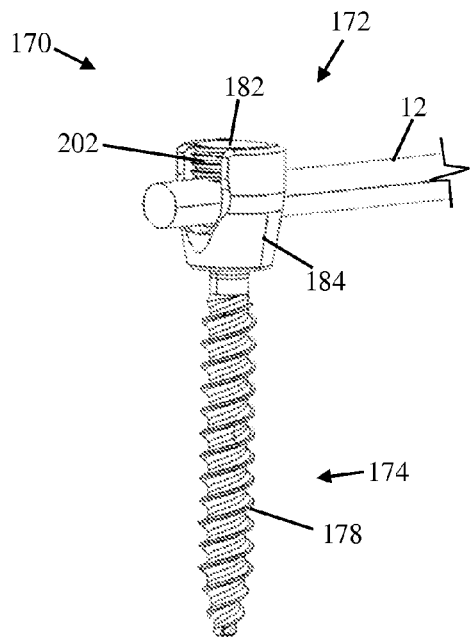
FIGS. 21 and 22 are perspective views of another example of a polyaxial bone anchor forming part of the vertebral fixation system of FIG. 1.
Figure 22:
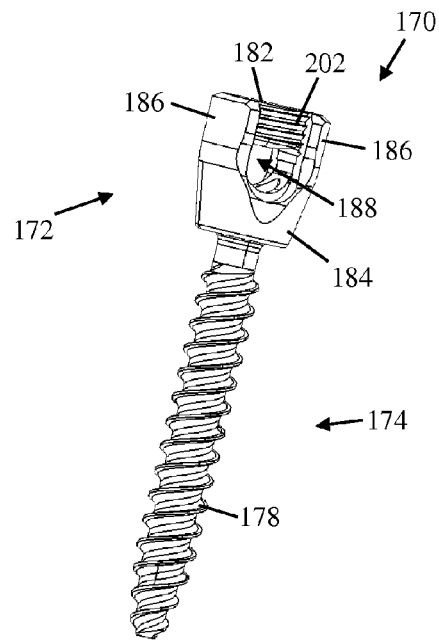
Figure 23:
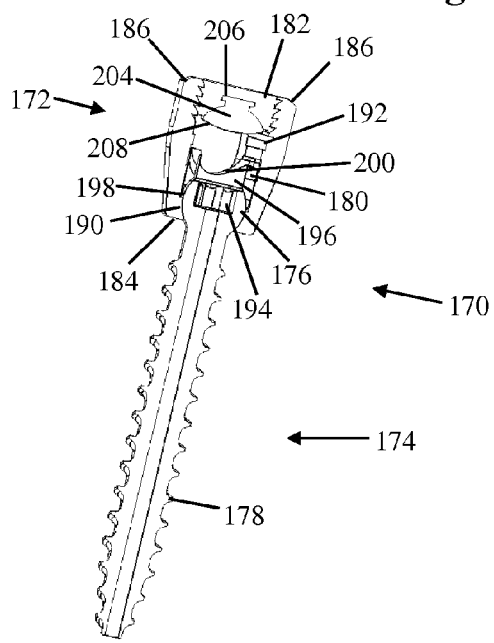
FIG. 23 is a perspective sectional view of the bone anchor of FIG. 21.
Figure 24:
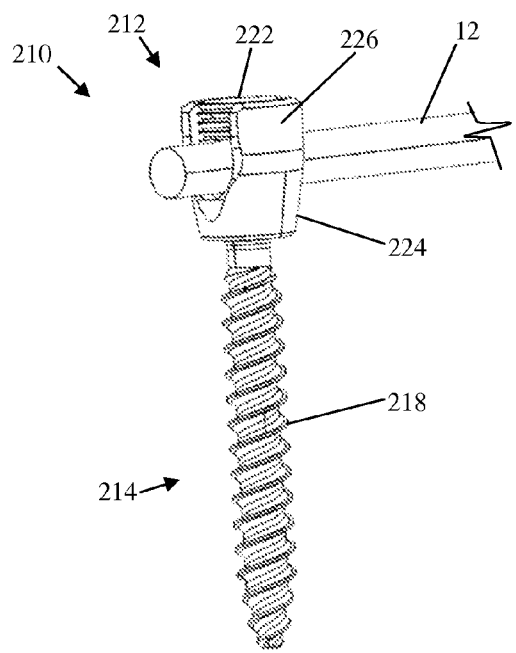
FIGS. 24 and 25 are perspective views of another example of a fixed angle bone anchor forming part of the vertebral fixation system of FIG. 1.
Figure 25:
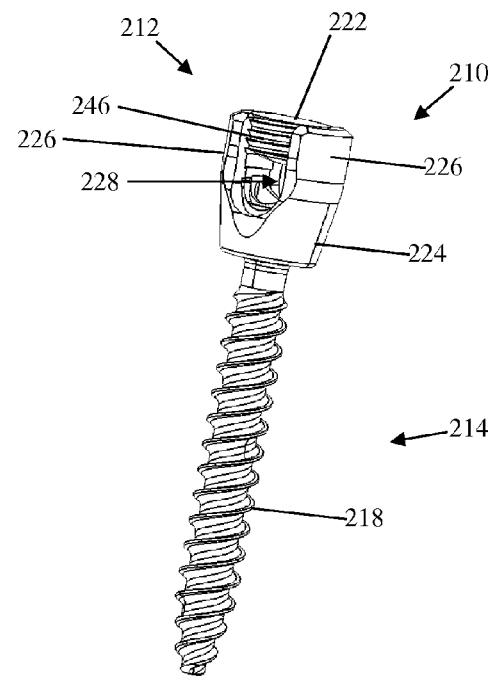
Figure 26:
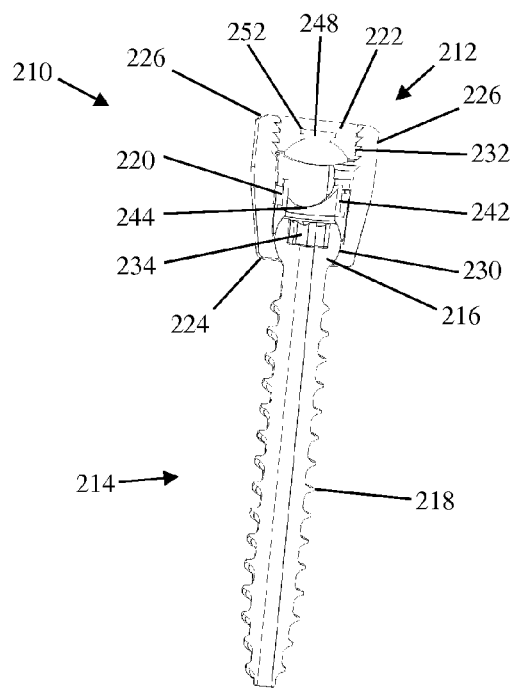
FIGS. 26 and 27 are perspective sectional views of the bone anchor of FIG. 24.
Figure 27:
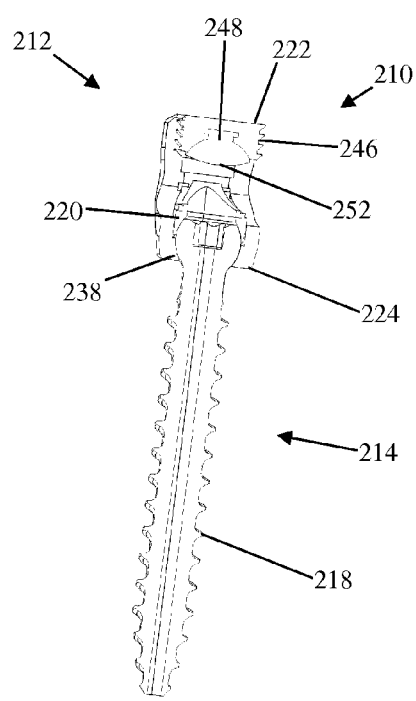

FIGS. 21-23 illustrate another example of a bone anchor configured for use with the vertebral fixation system 10 described above. By way of example, the bone anchor 170 is a polyaxial screw having a housing 172 for capturing and locking therein a spinal rod 12, a shank 174 including a generally spherical head 176 and a thread feature 178 suitable for stable fixation to vertebral bone, a seat member 180, and a locking element 182 configured for locking the spinal rod 12 within the housing 172.

The housing 172 has a base 184 that mates with the shank 174 and a pair of upstanding arms 186 separated by and partially defining a rod channel 188 sized and configured to receive the spinal rod 12 therein. The base 184 includes a recess 190 having a concave surface sized and dimensioned to receive the spherical head 176 of the shank 174. The spherical head 176 is able to rotate and pivot within the recess 190 such that the shank 174 may be disposed at any number of a plurality of angles relative to the housing 172. The upstanding arms 186 include a locking element engagement feature 192 disposed on the interior face of each arm 186. The locking element engagement feature 192 mates with a complementary housing engagement feature 202 on the locking element 182, described in further detail below.

The shank 174 further includes a driver recess 194 positioned at the top of the head 176 such that the driver recess 194 is accessible from the rod channel 138 prior to insertion of the locking element 182. The driver recess 194 is configured to engage a driver instrument (not shown) to enable implantation of the bone anchor 170 into a vertebral bone.

The seat member 180 is generally cylindrical in shape and has a lumen 146 extending longitudinally therethrough to allow passage of a driver instrument so that the driver instrument may engage the driver recess 194 of the shank 174. The lower portion of the lumen 196 has a concave surface 198 configured to receive and engage at least a portion of the generally spherical head 176 of the shank 174. The seat member 180 also includes a rod seat 200 in the form of a pair of opposing concave recesses on the upper portion of the seat member 180. The concave surfaces 200 are configured to engage the generally cylindrical spinal rod 12 and provide a seat for the spinal rod 12.

The locking element 182 is attachable to the housing 172 after the spinal rod 12 has been seated within the rod channel 188. In the example presently described, the locking element 182 comprises a setscrew having a housing engagement feature 202 and a rod engagement insert 204. The housing engagement feature 202 complementarily engages the locking element engagement feature 192 of the upstanding arms 186. The rod engagement insert 204 is a block of material sized and dimensioned to snugly fit within a recess 206 formed within the locking element 182 and having a convex surface 208 that forms the upper boundary of the rod channel 188 when the locking element 182 is mated with the housing 172. The convex surface 208 is configured to engage the generally cylindrical spinal rod 12 and exert a force on the spinal rod 12 to enable the frictional lock. By way of example, the locking element 182 is made of a rigid material (e.g. titanium). Significantly, the rod engagement insert 204 of the instant example may be formed of a semi-rigid elastomeric material that allows for some movement (e.g. vertical shifting, axial rotation, pivoting, and/or translation) of the spinal rod 12 within the housing 172 while maintaining a frictional association with the spinal rod 12 (and thus preventing unrestricted movement of the rod). The rod engagement insert 204 is secured within the recess 206 via a physical barrier (i.e. flange and lip interaction) however other methods of securing the rod engagement insert 204 within the recess 206 are possible.

In use, after the spinal rod 12 has been seated within the rod channel 188, the locking element 182 is inserted between the upstanding arms 186 such that the housing engagement feature 202 on the locking element 182 engages the locking element engagement features 192 on each of the upstanding arms 186. The locking element 182 is then advanced via rotation to exert a force on the spinal rod 12 and frictionally lock the spinal rod 12 within the housing 172 (and between the locking element 182 and the rod seat 200). After implantation, the semi-rigid nature of the elastomeric rod engagement insert 204 will allow the construct to absorb some force and experience some potential alignment correction that may occur from natural shifting of the patient's body, thereby potentially alleviating some conditions that may lead to junctional disease or failure (e.g. PJK, DJK, etc.).

FIGS. 24-27 illustrate another example of a bone anchor configured for use with the vertebral fixation system 10 described above. By way of example, the bone anchor 210 is a polyaxial screw having a housing 212 for capturing and locking therein a spinal rod 12, a shank 214 including a generally spherical head 216 and a thread feature 218 suitable for stable fixation to vertebral bone, a seat member 220, and a locking element 222 configured for locking the spinal rod 12 within the housing 212.

The housing 212 has a base 224 that mates with the shank 214 and a pair of upstanding arms 226 separated by and partially defining a rod channel 228 sized and configured to receive the spinal rod 12 therein. The base 224 includes a recess 230 having a concave surface sized and dimensioned to receive the spherical head 216 of the shank 214. The spherical head 216 is able to rotate and pivot within the recess 230 such that the shank 214 may be disposed at any number of a plurality of angles relative to the housing 212. The upstanding arms 226 include a locking element engagement feature 232 disposed on the interior face of each arm 226. The locking element engagement feature 232 mates with a complementary housing engagement feature 246 on the locking element 222, described in further detail below.

The shank 214 further includes a driver recess 234 positioned at the top of the head 216 such that the driver recess 234 is accessible from the rod channel 228 prior to insertion of the locking element 222. The driver recess 234 is configured to engage a driver instrument (not shown) to enable implantation of the bone anchor 210 into a vertebral bone.

The seat member 220 is identical to the seat member 130 described in reference to FIGS. 19 and 20. The seat member 220 is generally cylindrical in shape and has a lumen extending longitudinally therethrough to allow passage of a driver instrument so that the driver instrument may engage the driver recess 234 of the shank 214. The lower portion of the lumen has a concave surface 238 configured to receive and engage at least a portion of the generally spherical head 216 of the shank 214. The seat member 220 also includes a pair of opposing concave recesses on the upper portion of the seat member. When properly assembled, the concave recesses are aligned with and form part of the rod channel 228 for receiving the spinal rod 12.

The seat member 220 further includes a rod seat 242 disposed within the upper portion of the lumen. The rod seat 242 is a block of material sized and dimensioned to snugly fit within the lumen and having a pair of concave surfaces 244 that form part of the lower portion of the rod channel 228. The concave surfaces 244 are configured to engage the generally cylindrical spinal rod 12 and provide a seat for the spinal rod 12. Significantly, the rod seat 242 of the instant example may be formed of a semi-rigid elastomeric material that allows for some movement (e.g. vertical shifting, axial rotation, pivoting, and/or translation) of the spinal rod 12 within the housing 212 while maintaining a frictional association with the spinal rod 12 (and thus preventing unrestricted movement of the rod). By way of example, the rod seat 242 is secured within the lumen via a physical barrier interaction (i.e. a flange on the rod seat that is received within a recess disposed within the lumen).

The locking element 222 is attachable to the housing 212 after the spinal rod 12 has been seated within the rod channel 228. In the example presently described, the locking element 222 comprises a setscrew having a housing engagement feature 246 and a rod engagement insert 248. The housing engagement feature 246 complementarily engages the locking element engagement feature 232 of the upstanding arms 226. The rod engagement insert 248 is a block of material sized and dimensioned to snugly fit within a recess 250 formed within the locking element 222 and having a convex surface 252 that forms the upper boundary of the rod channel 188 when the locking element 222 is mated with the housing 212. The convex surface 252 is configured to engage the generally cylindrical spinal rod 12 and exert a force on the spinal rod 12 to enable the frictional lock. By way of example, the locking element 222 is made of a rigid material (e.g. titanium). Significantly, the rod engagement insert 248 of the instant example may be formed of a semi-rigid elastomeric material that allows for some movement (e.g. vertical shifting, axial rotation, pivoting, and/or translation) of the spinal rod 12 within the housing 212 while maintaining a frictional association with the spinal rod 12 (and thus preventing unrestricted movement of the rod). The rod engagement insert 248 is secured within the recess 250 via a physical barrier (i.e. flange and lip interaction) however other methods of securing the rod engagement insert 248 within the recess 250 are possible.

In use, after the spinal rod 12 has been seated within the rod channel 228, the locking element 222 is inserted between the upstanding arms 226 such that the housing engagement feature 246 on the locking element 222 engages the locking element engagement features 232 on each of the upstanding arms 226. The locking element 222 is then advanced via rotation to exert a force on the spinal rod 12 and frictionally lock the spinal rod 12 within the housing 212 (and between the locking element 222 and the rod seat 242). After implantation, the semi-rigid nature of the elastomeric rod seat 242 and the elastomeric rod engagement insert 248 will allow the construct to absorb some force and experience some potential alignment correction that may occur from natural shifting of the patient's body, thereby potentially alleviating some conditions that may lead to junctional disease or failure (e.g. PJK, DJK, etc.).

Figure 28:
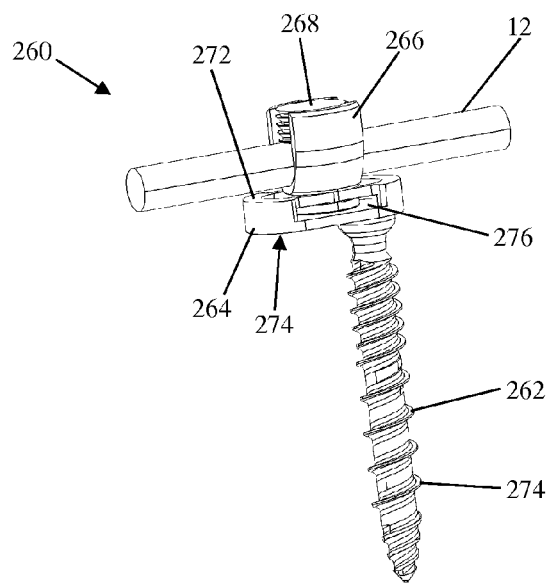
FIGS. 28-30 are perspective views of an example of a bone anchor having a translating tulip configured for use with and forming part of the vertebral fixation system of FIG. 1.
Figure 29:
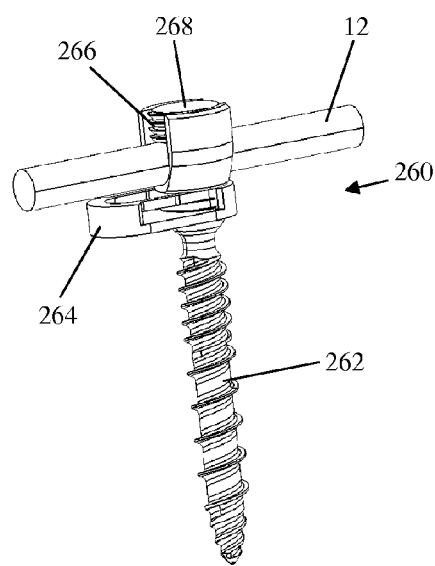
Figure 30:
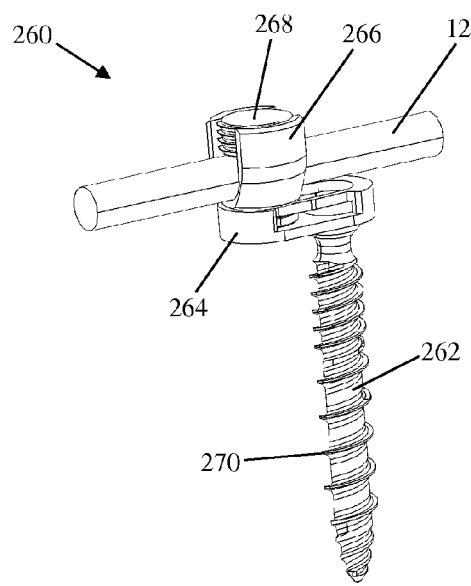
Figure 31:
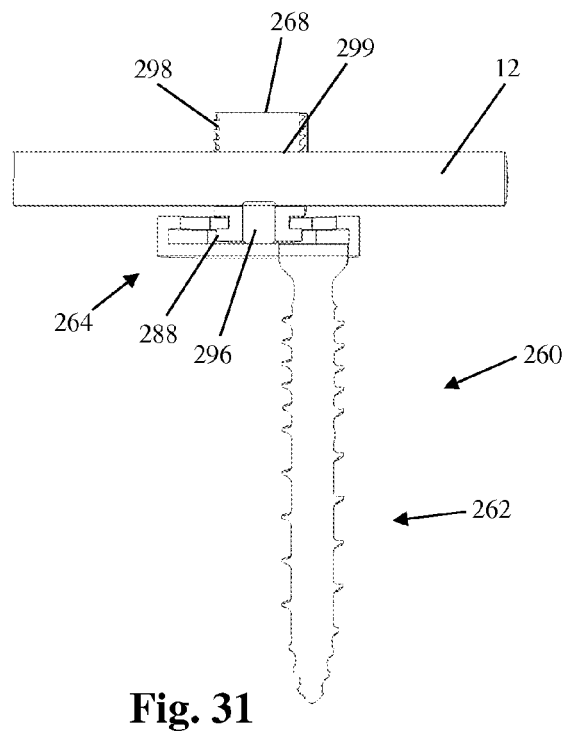
FIGS. 31 and 32 are sectional views of the bone anchor of FIG. 28.
Figure 32:
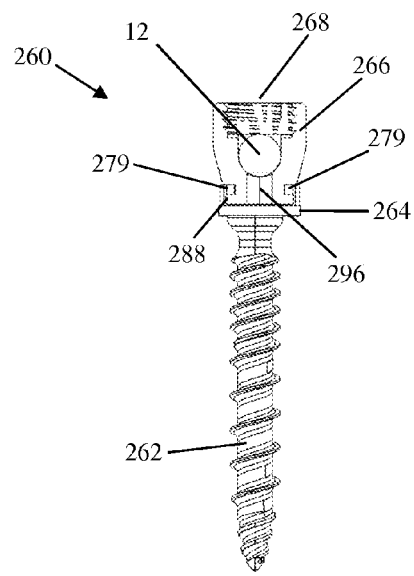
Figure 33:
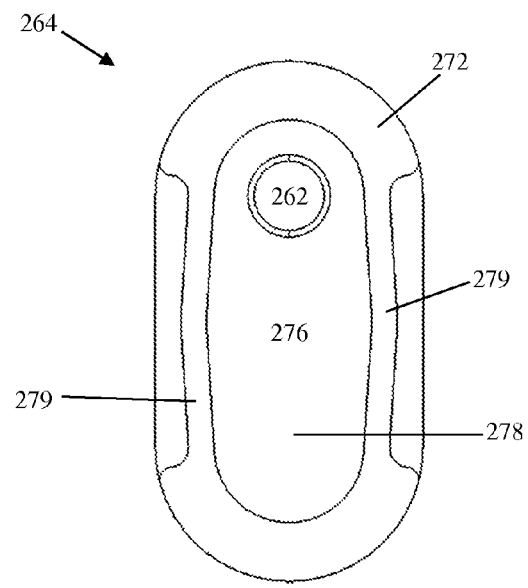
FIG. 33 is a plan view of a translation base forming part of the bone anchor of FIG. 28.

FIGS. 28-35 illustrate another example of a bone anchor assembly configured for use with the vertebral fixation system 10 described above. By way of example, the bone anchor assembly 260 includes a bone anchor 262, a translation body 264, a rod-receiving member 266, and a locking element 268. As will be explained below, the bone anchor assembly 260 is semi-adjustable after implantation (e.g. allows for controlled motion) in that the rod-receiving member 266 has some freedom to translate and/or rotate relative to the translation body 264 to accommodate natural shifting that may occur. By way of example, FIGS. 28-30 illustrate the bone anchor assembly 260 with the rod-receiving member 266 in three different translational positions.

The bone anchor 262 extends generally perpendicularly from the bottom surface of the translation body 264 and has a thread feature 270 suitable for stable fixation to vertebral bone. The translation body 264 has a generally elliptical footprint (illustrated in FIG. 33) however other shapes are possible. The translation body 264 has a top surface 272, a bottom surface 274, and a translation surface 276 configured to engage the rod-receiving member 266 and allow translation in a proximal-distal direction. The top surface 272 is generally planar however other shapes including but not limited to convex are possible. The top surface 272 has an elongated recess 278 having a T-shaped cross-section formed therein that limits the degree of translation. By way of example, the elongated recess 278 may be generally elliptical in shape but may also be tapered in that it is wider in the center of the recess than it is at either end. This tapered shaped functions to provide greater resistance to incremental translation as the rod-receiving member 266 approaches the outer ends of the recess 278 in either direction. The recess 278 further includes a pair of overhangs 279 that give the recess 278 its T-shaped cross-section and also function to retain the cylindrical flange 288 of the rod-receiving member 266 within the recess 278. The translation surface 276 comprises the bottom surface of the elongated recess 278 and may be planar or slightly convex.

Figure 34:
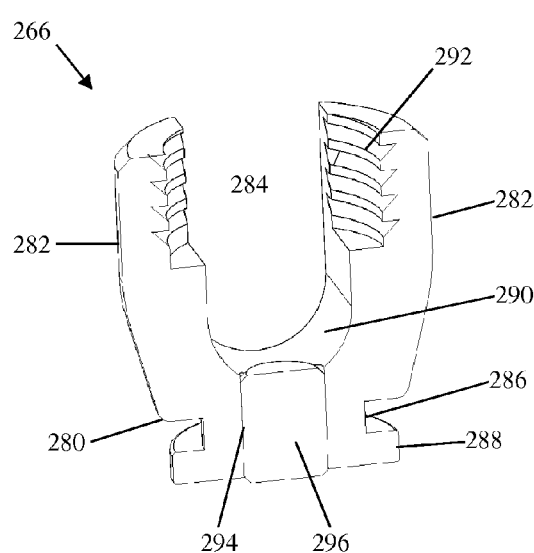
FIGS. 34 and 35 are sectional and perspective views, respectively, of a rod-receiving member forming part of the bone anchor of FIG. 28.
Figure 35:
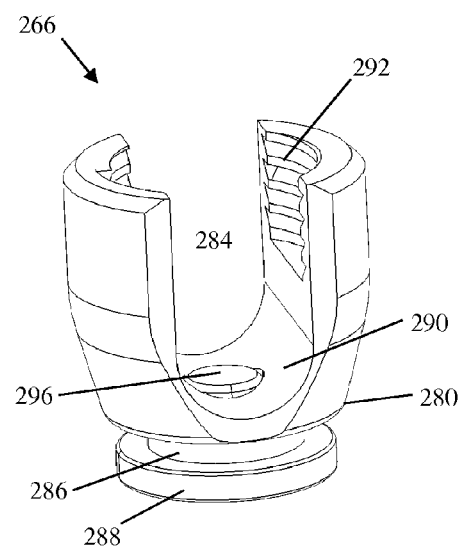
Figure 39:
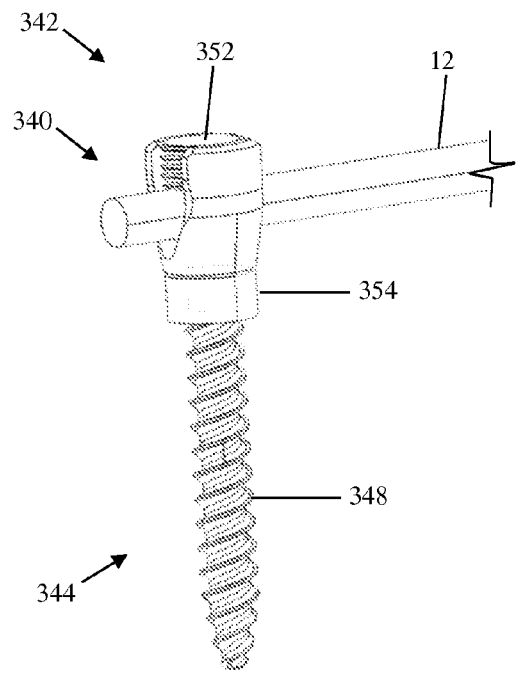
FIGS. 39 and 40 are perspective view of still another example of a bone anchor suitable for use with the vertebral fixation system of FIG. 1.
Figure 40:
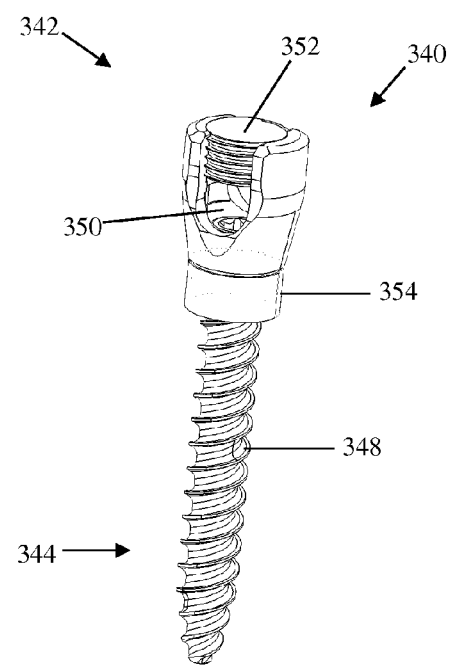
Figure 41:
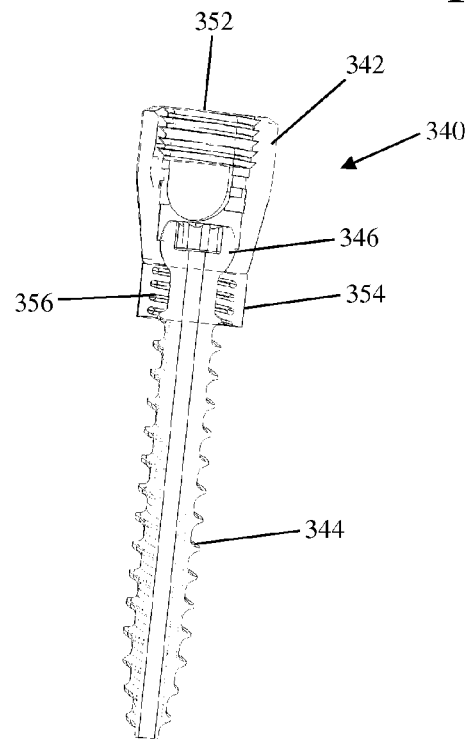
FIG. 41 is a sectional view of the bone anchor of FIG. 39.

Referring to FIGS. 34 and 35, the rod-receiving member 266 includes a base 280 and a pair of upstanding arms 282 separated by a rod channel 284. The base 280 includes a protrusion 286 extending away from the base 280 and a cylindrical flange 288 positioned a the end of the protrusion 286. The protrusion 286 has a generally cylindrical shape and has a diameter that is less than the diameter of the cylindrical flange 288. The result is that the protrusion 286 and flange 288 when taken together have a generally T-shaped cross section. The protrusion 286 and flange 288 fit within the recess 278 of the fixation body 264 and are configured to allow multiple degrees of movement of the rod-receiving member 266 relative to the fixation body 264. More specifically, the cylindrical shapes of both the protrusion 286 and flange 288 allow axial rotation of the rod-receiving member, and a generally planar bottom surface 290 of the flange 288 allows for smooth translation of the flange 288 (and thus the rod-receiving member 266) within the recess 264. The upper surface 290 of the base 280 is a concave, semi-cylindrical surface having a generally arcuate cross-section. The upper surface 290 forms the distal end of the rod channel 284 and forms a cradle that receives the spinal rod 12 during implantation. The upstanding arms 282 are equipped with a locking element engagement feature 292 disposed on the interior face of each arm 282. The locking element engagement feature 292 mates with a housing engagement feature 298 on the locking element 268.

The base 280 has a hollow lumen 294 formed therein and configured to receive an elastomeric plug therein. In the example shown in FIGS. 34 and 35, both the hollow lumen 294 and the elastomeric plug 296 have generally cylindrical cross sections, however other shapes are possible. The elastomeric plug 296 has a length that is at least slightly greater than the length of the hollow lumen 294 so that the ends of the elastomeric plug 296 are in continuous contact with both the spinal rod 12 and the translation surface 276 of the translation body 264. After implantation, the semi-rigid nature of the elastomeric plug 296 will allow the construct to absorb some force and experience some potential alignment correction that may occur from natural shifting of the patient's body, thereby potentially alleviating some conditions that may lead to junctional disease or failure (e.g. PJK, DJK, etc.).

The locking element 268 is attachable to the upstanding arms 282 after the spinal rod 12 has been seated within the rod channel 284. In the example presently described, the locking element 268 comprises a setscrew having a housing engagement feature 298 and a rod engagement surface 299. The housing engagement feature 298 complementarily engages the locking element engagement feature 292 of the upstanding arms 282. The rod engagement surface 299 is configured to engage the spinal rod 12 and may be planar, convex, or concave. By way of example, the locking element 268 is made of a rigid material (e.g. titanium).

FIGS. 36-38 illustrate an example utilizing tethers connected to bone anchors and/or rods to strengthen, reconstruct, and/or otherwise emulate ligaments that may have been damaged or removed during implantation of the vertebral fixation system 10. For example, a tether connected to a bone anchor may be wrapped around the facet, transverse process, lamina, rib and/or spinous process to provide further stability to the construct. As another example, a tether may be attached to a rod at or near the proximal terminus of the vertebral fixation system 10 in lieu of bone screws to alleviate or eliminate factors that may cause junctional disease or failure (e.g. PJK, DJK, etc.).

FIG. 36 illustrates an example of a bone anchor 300 with an attached tether suitable for use with the vertebral fixation system 10. By way of example, the bone anchor 300 may be either a fixed angle screw or polyaxial screw. The bone anchor 300 includes a housing 302 for capturing and locking therein a spinal rod 12, a shank 304 including a thread feature 306 suitable for stable fixation to vertebral bone, and a locking element 308 configured for locking the spinal rod 12 within the housing 302. The bone anchor 300 is substantially similar to the various examples of bone anchors described throughout this disclosure such that repeat description of the housing 302, shank 304, and locking element 308 beyond what is necessary to describe the additional tether feature specific to this example embodiment is not necessary. It is to be understood that any feature of any other example embodiment described herein may be included in this (and any other) example embodiment without reservation either alone or in combination.

The housing 302 has a pair of upstanding arms 310 separated by and partially defining a rod channel sized and configured to receive the spinal rod 12 therein. At least one of the upstanding arms 310 includes a tether connector 312 extending outwardly away from the arm 310 and configured to fixedly receive a tether 314 therein. By way of example, the tether connector 312 comprises a post member having a lumen 316 formed therein that is sized to receive at least a portion of the tether 314. The tether 314 may be formed of any material suitable for medical use. For example, the tether may be made from allograft tendon, autograft tendon, braided, woven, or embroidered polyethylene, braided, woven, or embroidered polyester, PEEK, or PEKK. In some instances the tether 314 may be formed of elastic material. The tether 314 of the instant example has a stop element 318 attached to or otherwise forming the proximal end of the tether 314. The stop element 318 buffers against the tether connector 312 and acts as a physical barrier to prevent the proximal end of the tether 314 from passing through the lumen 316. In this way the tether 314 is secured to the tether connector 312. By way of example, the stop element may be formed by a knot, a clamp, or a crimp. Additionally the stop element may be in the form of a connection loop created when the proximal end of the tether is reattached to itself (e.g. via clamp, crimp, adhesive, braiding, weaving, and/or embroidery) distal of the tether connector 312. Other attachment methods of securing the tether 314 to the tether connector 312 are possible, including but not limited to adhesive, spot welding, set screw, and the like. The tether 314 may be formed of any length necessary to secure the bone anchor 300 to surrounding bone structure. By way of example, the tether may be wrapped around (or, through a hole formed therein) one or more of a lamina(s), transverse process(es), spinous process(es), and rib(s). After wrapping around the bone, the tether may be attached back to itself (e.g. via knot, clamp, crimp, etc. . . . ), a second tether connector on the housing 302, or a tether connector on another bone anchor (e.g. a contralateral anchor) or alternate connector, such as the rod connector 320 described below. Alternatively, the tether may be anchored directly to the lamina(s), transverse process(es), spinous process(es), or rib(s) (for example, with a suture anchor, staple, or similar device).

FIG. 37 illustrates an example of a rod attachment 320 with attached tether suitable for use with the vertebral fixation system 10. The rod attachment 320 includes a housing 322 having a lumen 324 extending longitudinally therethrough configured to receive at least a portion of the spinal rod 12. By way of example, the housing 322 includes one side comprising a generally planar surface 326 and another side comprising a generally arcuate surface 328. The generally planar surface 326 includes at least one aperture 330 for receiving a locking element 332. In the instant example, the generally planar surface 326 includes a pair of apertures 330 and thus the rod attachment 320 has a pair of locking elements 332. The locking elements 332 are substantially similar to the locking elements described in the various examples above and further description need not be repeated. The rod attachment 320 further includes a tether connector 334 extending outwardly and configured to fixedly receive a tether 336 therein. The tether connector 334 comprises a post member having a lumen 335 formed therein that is sized to receive at least a portion of the tether 336. The tether 336 of the instant example has a stop element 338 attached to or otherwise forming the proximal end of the tether 336. By way of example, the stop element may be formed by a knot, a clamp, or a crimp. Additionally the stop element 338 may be in the form of a connection loop created when the proximal end of the tether is reattached to itself (e.g. via clamp, crimp, adhesive, braiding, weaving, and/or embroidery) distal of the tether connector 334. Other attachment methods of securing the tether 336 to the tether connector 334 are possible, including but not limited to adhesive, spot welding, set screw, and the like. The tether 336 may be formed of any length necessary to secure the rod, via rod connector 320, to surrounding bone structure. By way of example, the tether may be wrapped around (or, through a hole formed therein) one or more of a lamina(s), transverse process(es), spinous process(es), and rib(s). After wrapping around the bone, the tether may be attached back to itself (e.g. via knot, clamp, crimp, etc. . . . ), a second tether connector on the housing 322, or a tether connector on another bone anchor or rod connector connector, such as the rod connector 320 described below. Alternatively, the tether may be anchored directly to the lamina(s), transverse process(es), spinous process(es), or rib(s) (for example, with a suture anchor, staple, or similar device).

FIG. 38 illustrates the bone anchor 300 and rod attachment 320 in use after implantation in a human spine. By way of example, as shown the tethers are wrapped around a lamina, transverse process, and a spinous process. It will be appreciated that the tether may be wrapped around one of, or any combination of, one or more lamina, transverse processes, spinous processes, and ribs.

FIGS. 39-44 illustrate another example of a bone anchor 340 suitable for use with the vertebral fixation system 10. In the embodiment shown by way of example in the attached Figs., the bone anchor 340 is substantially similar to any of the polyaxial bone screw example embodiments described above such that features described above may be applied to this example without reservation either alone or in combination. The bone anchor 340 includes a housing 342 for capturing and locking therein a spinal rod 12, a shank 344 including a generally spherical head 346 and a thread feature 348 suitable for stable fixation to vertebral bone, a seat member 350, and a locking element 352 configured for locking the spinal rod 12 within the housing 342.

The bone anchor 340 further includes a collar 354 positioned at the top of the shank 344 just below the head 346 such that the collar 354 is flushly engaged with the housing 342. By way of example only, the collar 354 may be composed of an elastomeric material and may also have a spring 356 disposed therein that is biased toward the housing 342. The collar 354 functions to convert the otherwise fixed relationship between shank and head upon locking of a rod with a setscrew into a limited range permanent polyaxial bone screw. Once the bone anchor 340 has been implanted into the spine as a part of the vertebral fixation system 10 it may experience realignment pressure (of the type that causes DJK and PJK). Under such a circumstance, the elastomeric collar 354 and/or spring 356 are capable of allowing controlled movement of the housing 342, for example adjustment of the angle formed between the housing member 342 and shank 344, controlled minimal translation along the spinal rod 12, and/or further compression of the collar 354 if adjustment is needed in that direction.

In some instances it may be beneficial if the spinal rod itself was capable of compression, distraction, and/or rotation in response to realignment pressure. FIGS. 42-44 illustrate the bone anchor 340 used with one example of a flexible rod 790. By way of example, the flexible rod 790 includes an interior rod 792, a spring coil 794, and an elastomeric sheath 796. The interior rod 792 has a narrow diameter and may be composed of any material that allows for some flexibility (e.g. Nitinol, PEEK, PEKK, etc.). The spring coil 794 is disposed around the interior rod 792 and may extend beyond the proximal terminus of the interior rod 792. The elastomeric sheath 796 is disposed around the interior rod 792 and the spring coil 794 and may extend the same length as the spring coil 794. The interior rod 792 gives the flexible rod 790 some rigidity, while the spring coil 794 functions to allow for compression, distraction and rotational movement of the flexible rod 790. The elastomeric sheath 796 holds the spring coil 794 in place and also allows for controlled compression, distraction, and rotational movement of the flexible rod 790. It should be noted that the locking element 352 locks the flexible rod 790 within the housing 342 but does not exert pressure to the point of compressing the spring coil 794 within the flexible rod 790.

FIGS. 45-48 illustrate an example of a transition apparatus 360 configured for use with the vertebral fixation system 10 described herein. The purpose of the transition apparatus 360 is to gradually reduce the rigidity of the fixation construct as it transitions from instrumented to non-instrumented vertebra. One advantage associated with the transition apparatus 360 is it reduces the need for muscle stripping along the patient's back and therefore may leave intact those anatomical structures that naturally help to prevent outcomes such as DJK or PJK.

Figure 45:
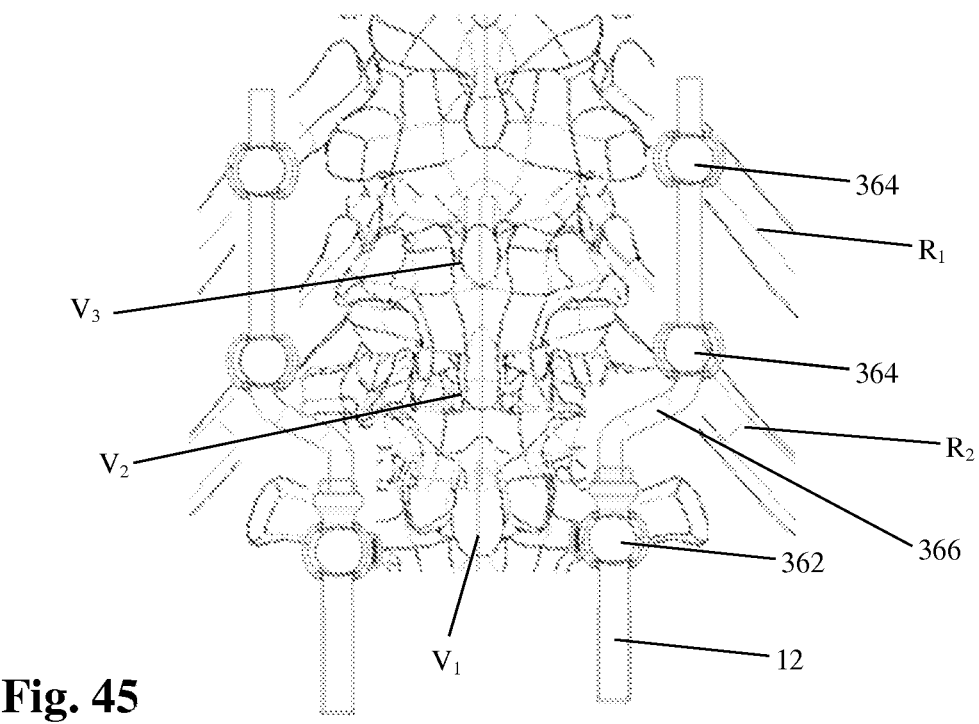
FIG. 45 is a plan view of a portion of a spine with an implanted transition apparatus suitable for use with the vertebral fixation system of FIG. 1.
Figure 46:
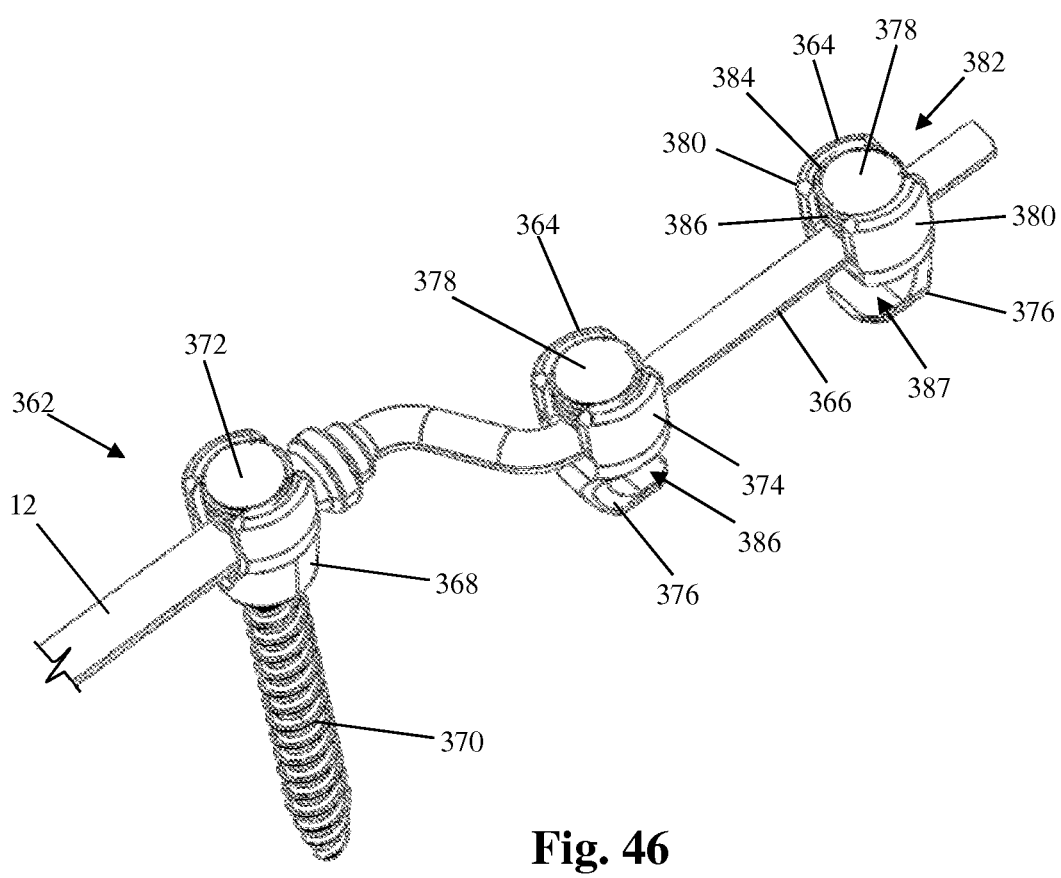
FIG. 46 is a perspective view of the transition apparatus of FIG. 45.
Figure 47:
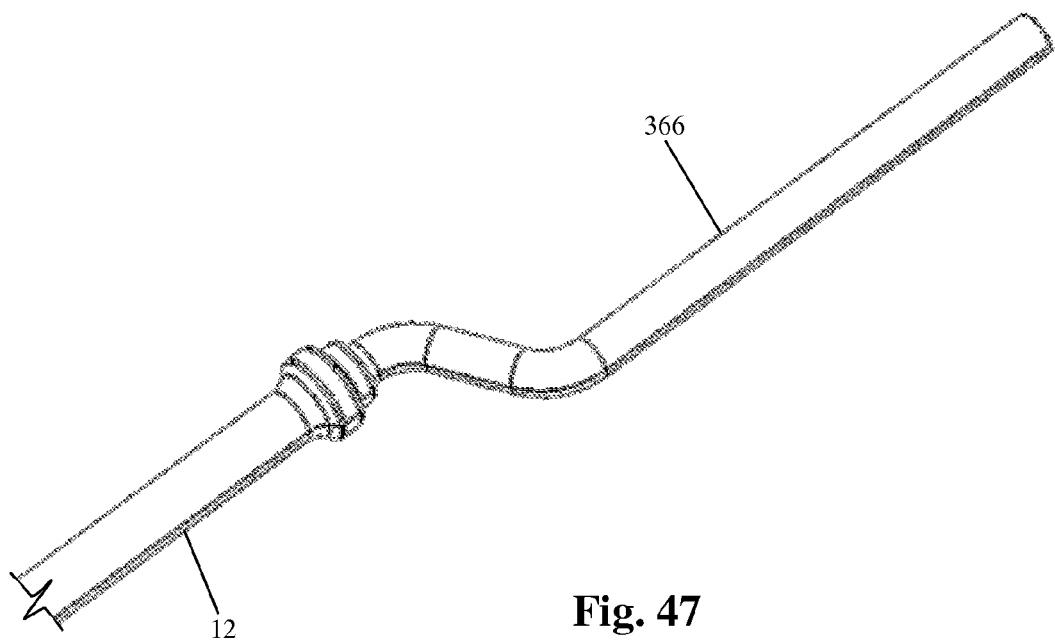
FIG. 47 is a perspective view of a rod-cord hybrid forming part of the transition apparatus of FIG. 45.
Figure 48:
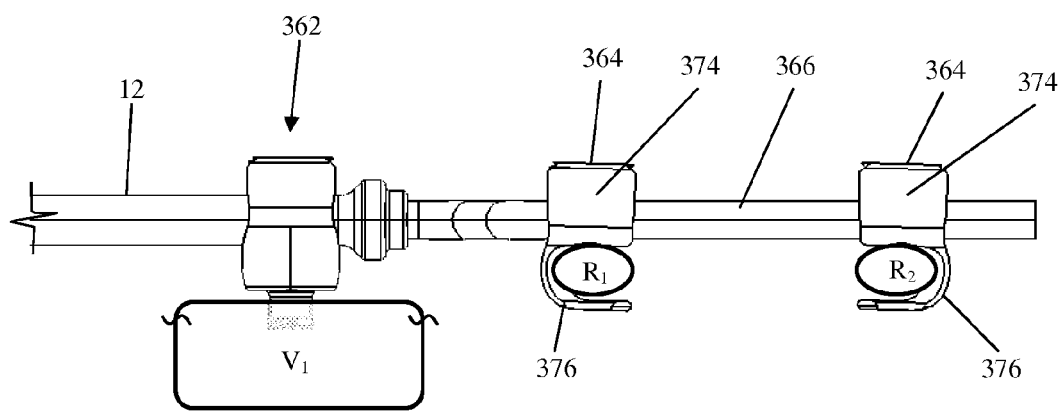
FIG. 48 is a side plan view of the transition apparatus of FIG. 45.
Figure 49:
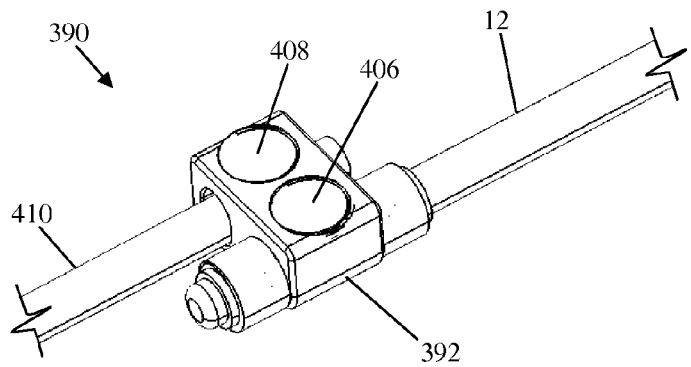
FIG. 49 is a perspective view of another example of a transition apparatus suitable for use with the vertebral fixation system of FIG. 1.
Figure 50:
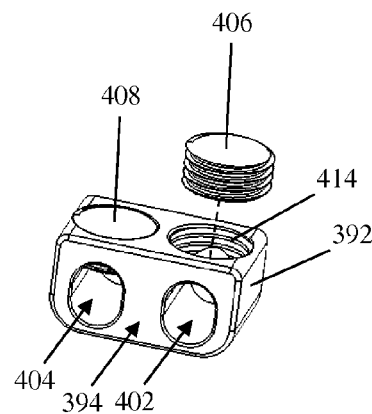
FIG. 50 is a perspective view of a housing unit forming part of the transition apparatus of FIG. 49.
Figure 51:
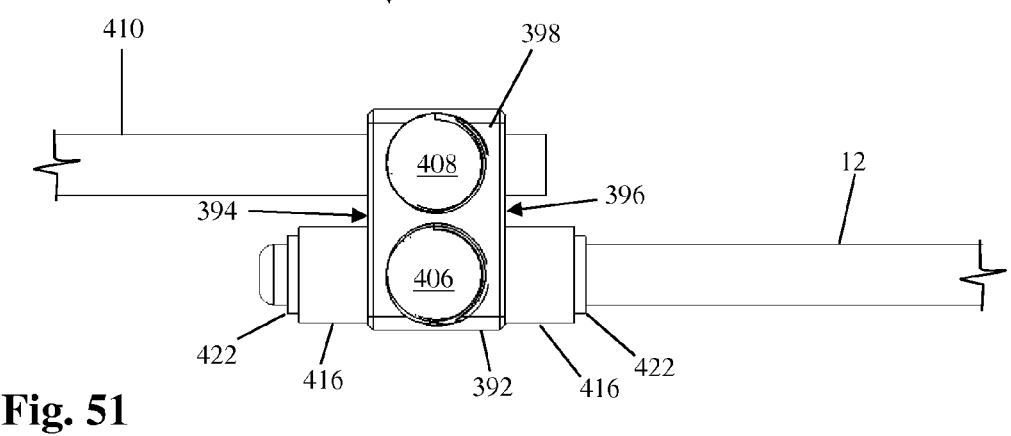
FIGS. 51 and 52 are plan and top sectional views, respectively, of the transition apparatus of FIG. 49.
Figure 52:
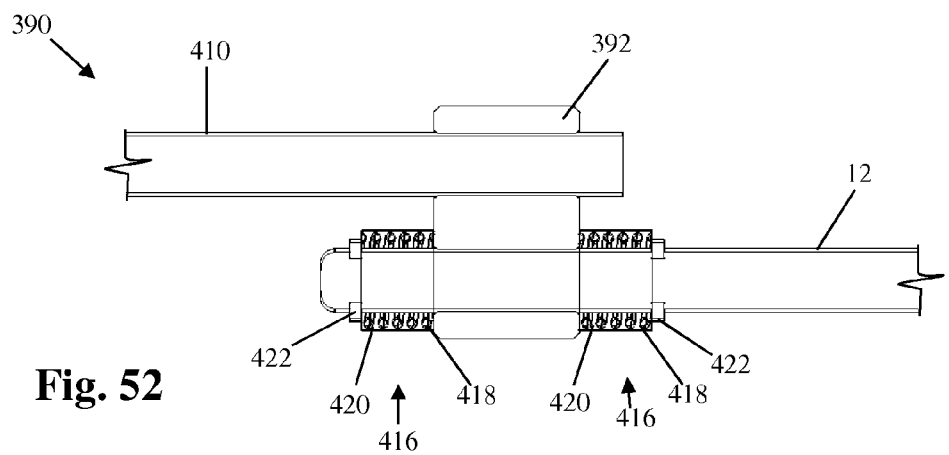
Figure 53:
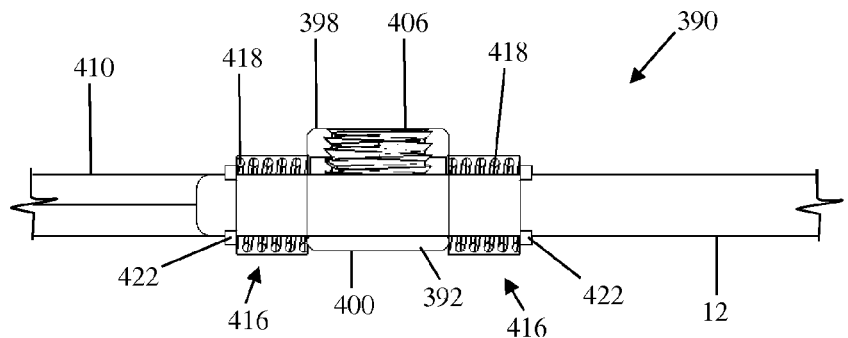
FIG. 53 is a side sectional view of the transition apparatus of FIG. 49.
Figure 54:
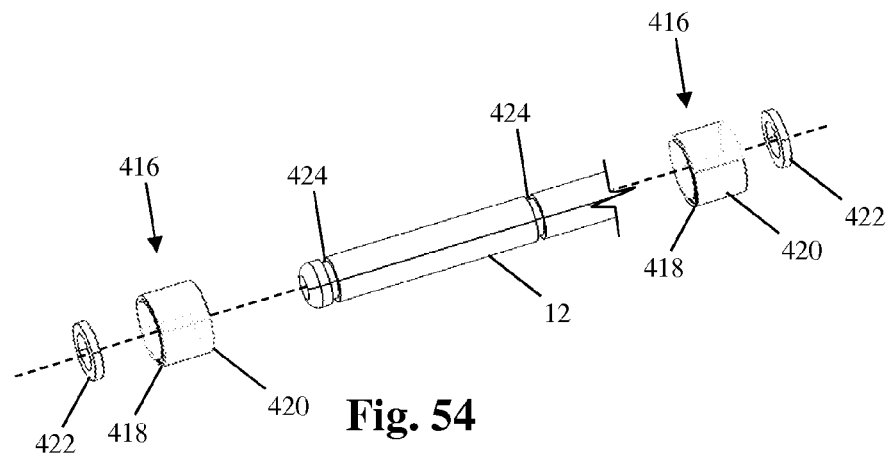
FIG. 54 is an exploded view of a spinal rod terminus forming part of the transition apparatus of FIG. 49.
Figure 55:
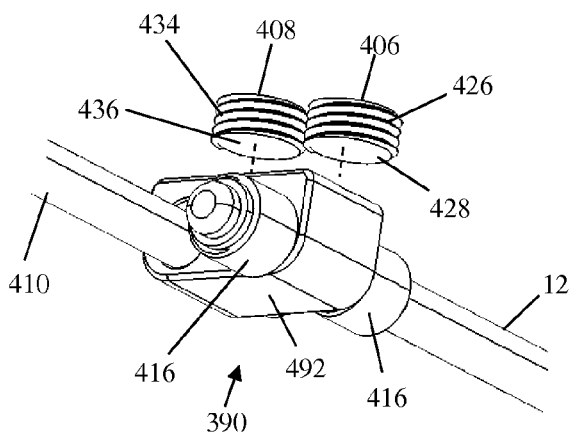
FIGS. 55 and 56 are perspective views of the transition apparatus of FIG. 49.
Figure 56:
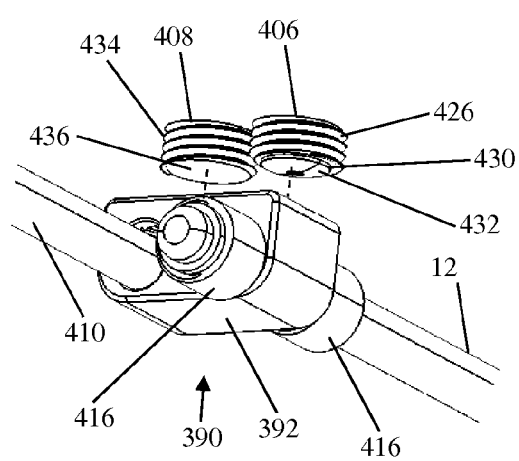
Figure 57:
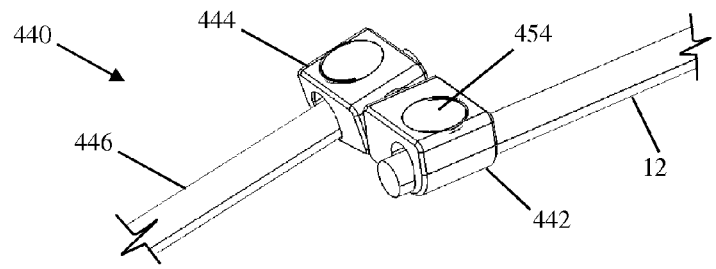
FIG. 57 is a perspective view of yet another transition apparatus suitable for use with the vertebral fixation system of FIG. 1.
Figure 58:
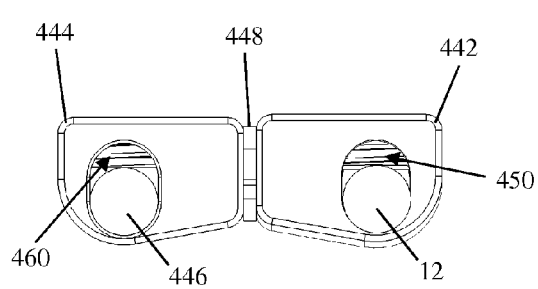
FIGS. 58 and 59 are plan views of the transition apparatus of FIG. 57.
Figure 59:
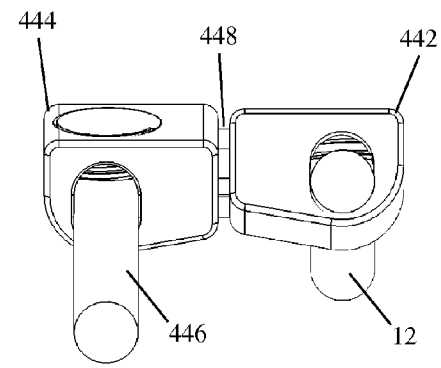
Figure 60:
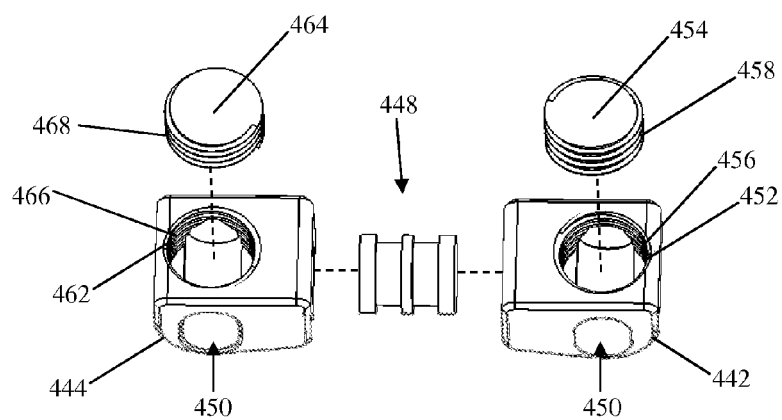
FIG. 60 is an exploded perspective view of the transition apparatus of FIG. 57.
Figure 61:
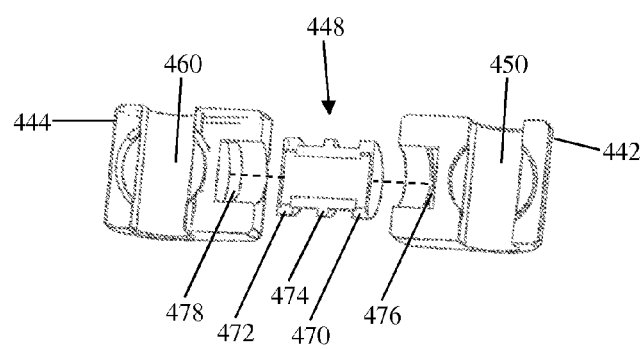
FIG. 61 is an exploded sectional view of the transition apparatus of FIG. 57.

FIG. 45 illustrates the transition apparatus 360 implanted in a segment of the spine. The transition apparatus 360 includes a bone anchor 362, one or more bone hooks 364, and a flexible cord 366. The bone anchor 362 includes a housing 368 for receiving the spinal rod 12, a shank 370, and a locking element 372 for securing the spinal rod 12 within the housing 368. The bone anchor 362 may be one of any of the bone screw example embodiments described above such that any and all features described above may be applied to this example without reservation either alone or in combination, and further discussion of the bone screw 362 is not necessary.

The bone hook 364 includes a housing 374, a generally curved hook member 376 extending from the base of the housing 374, and a locking element 378. The housing 374 includes a pair of upstanding arms 380 separated by and forming part of a rod channel 382. The upstanding arms 380 include a locking element engagement feature 384 disposed on the interior face of each arm 380. The locking element engagement feature 384 mates with a complementary housing engagement feature 386 on the locking element 378 to secure the flexible cord 366 within the rod channel 382. The generally curved hook member 376 is has a concave curvature that forms a cavity 386 dimensioned to receive a bone segment. By way of example only, the bone hooks 364 of the present example are configured to be used with rib bone, however other configurations are possible.

The flexible cord 366 may be composed of any material medically suitable for implantation into a human and sufficiently flexible to serve as a transition medium, including but not limited to autograft tendon, allograft tendon, braided polyethylene, PEEK, and PEKK. The flexible cord 366 is secured to the distal end of the spinal rod 12 via an attachment member 388.

In use, the bone anchor 362 is implanted into the proximal-most fully instrumented vertebral level $V_1$. The bone anchor 362 may have one or more of the features described above (e.g. elastomeric inserts in one or more of the rod seat and locking element, flexible collar, and the like). The spinal rod 12 terminates just proximally of the bone anchor 362 and transitions to a flexible cord 366. The path of the flexible cord 366 is directed laterally away from the spinal column and continues along a path determined by the placement of the bone hooks 364. For example, a first bone hook 364 may be secured to a rib $R_1$ associated with the first non-instrumented vertebral body $V_2$. A second bone hook 364 may be secured to a rib $R_2$ associated with the second non-instrumented vertebral body $V_3$. Since the cord path is away from the spine, less muscle tissue would need to be disturbed. And since the flexible cord 366 is flexible, it may be better suited to handle alignment shifts than a rigid construct.

FIGS. 49-56 illustrate another example of a transition apparatus configured for use with the vertebral fixation system 10 described herein. Transition apparatus 390 includes a housing 392 that generally has the form of a rectangular block having a leading surface 394, a trailing surface 396, a top surface 398, and a bottom surface 400, a first rod channel 402, a second rod channel 404, a first locking element 406, and a second locking element 408. The first rod channel 402 is sized and dimensioned to receive the proximal end of the spinal rod 12. The second rod channel 404 is configured to receive the distal end of a transition rod 410. The transition rod 410 is generally more flexible than the spinal rod 12 and serves to transitionally reduce the strain associated with the proximal terminus of the vertebral fixation system 10. The transition rod 410 may be composed of any suitable medical grade material capable of establishing a flexible connection, including but not limited to plastics (e.g. PEEK) or flexible metal (e.g. Nitinol). Additionally, the transition rod 410 may be in the form of a cylindrically shaped rod, an oval shape, a fluted configuration, a cord, or a tether.

The top surface 398 further includes a pair of apertures 412 for receiving the locking elements 406, 408 therein. The apertures 412 each have a locking element engagement feature 414 configured to engage the corresponding housing engagement features of the locking elements 406, 408. When inserted in the apertures 412, the locking elements 406, 408 are able to contact and lock in place the spinal rod 12 and transition rod 410, respectively.

The transition apparatus 390 further includes a pair of buffer elements 416 attached to the proximal end of the spinal rod 12, with one buffer element 416 attached to the spinal rod 12 on either side of the housing 392. The buffer element 416 includes a spring 418 or block of elastomeric material (not pictured) positioned within a sleeve 420. Locking rings 422 are provided within circumferential grooves 424 formed in the spinal rod 12 to provide a physical barrier for the buffer element 416 to ensure the buffer element 416 remains in place.

The first locking element 406 is attachable to the housing 392 after the spinal rod 12 has been seated within the rod channel 402. In the example shown in FIG. 55, the locking element 406 comprises a setscrew having a housing engagement feature 426 and a rod engagement surface 428. The housing engagement feature 426 complementarily engages the locking element engagement feature 414 of the housing 392. The rod engagement surface 428 is configured to engage the spinal rod 12 and may be planar, convex, or concave. By way of example, the locking element 406 is made of a rigid material (e.g. titanium). In the example shown in FIG. 56, the locking element 406 includes a rod engagement insert 430 comprising a block of material sized and dimensioned to snugly fit within a recess (not shown) formed within the locking element 406 and having a convex surface 432 that forms the upper boundary of the rod channel 402 when the locking element 406 is mated with the housing 392. The convex surface 432 is configured to engage the generally cylindrical spinal rod 12 and exert a force on the spinal rod 12 to enable the frictional lock. By way of example, the locking element 406 is made of a rigid material (e.g. titanium). Significantly, the rod engagement insert 430 of the instant example may be formed of a semi-rigid elastomeric material that allows for some movement (e.g. vertical shifting, axial rotation, pivoting, and/or translation) of the spinal rod 12 within the housing 392 while maintaining a frictional association with the spinal rod 12 (and thus preventing unrestricted movement of the rod). The rod engagement insert may be configured such that the limited movement occurs only upon surpassing a threshold pressure.

The second locking element 408 is attachable to the housing 392 after the transition rod 410 has been seated within the rod channel 404. The locking element 408 comprises a setscrew having a housing engagement feature 434 and a rod engagement surface 436. The housing engagement feature 434 complementarily engages the locking element engagement feature 414 of the housing 392. The rod engagement surface 436 is configured to engage the spinal rod 12 and may be planar, convex, or concave. By way of example, the locking element 408 is made of a rigid material (e.g. titanium).

The buffer element 416 allows for controlled translation/shifting of the spinal rod 12 within the housing 392 which will allow the construct to absorb some force and experience some potential alignment correction that may occur from natural shifting of the patient's body, thereby potentially alleviating some conditions that may lead to junctional disease or failure (e.g. PJK, DJK, etc.).

FIGS. 57-61 illustrate another example of a transition apparatus configured for use with the vertebral fixation system 10. The transition apparatus 440 of the present example generally comprises a parallel rod connector with multiple degrees of freedom of movement. The transition apparatus 440 includes a first housing 442 configured for receiving the spinal rod 12 and a second housing 444 configured for receiving a transition rod 446. The first housing 442 and second housing 444 are connected via a pivot connector 448. The first housing 442 is offset from the second housing 444 such that a longitudinal axis extending through the first rod channel 450 is parallel to, but not aligned with, a longitudinal axis extending through the second rod channel 460.

The first housing includes a first rod channel 450 extending therethrough that is sized and configured to receive the proximal portion of the spinal rod 12. The rod channel 450 has an elliptical cross-section to allow for some constrained motion of the spinal rod 12 within the rod channel 450 after implantation. The first housing 442 further includes an aperture 452 adjacent the rod channel 450 for receiving a locking element 454. The aperture 452 includes a locking element engagement feature 456 configured to engage the corresponding housing engagement feature 458 of the locking element 454. When inserted in the aperture 452, the locking element 454 is able to contact and lock in place the spinal rod 12 while allowing for some controlled movement within the rod channel 450. The locking element 454 comprises a setscrew having a housing engagement feature 458 and a rod engagement surface. The housing engagement feature 458 that complementarily engages the locking element engagement feature 456 of the first housing 442. The rod engagement surface is configured to engage the spinal rod 12 and may be planar, convex, or concave. Although not shown, the locking element 454 may alternatively be equipped with a rod engaging insert comprising a block of elastomeric material (for example) as shown and described in various example embodiments disclosed above.

The second housing 444 includes a second rod channel 460 extending therethrough that is sized and configured to receive a distal portion of the transition rod 446. The rod channel 460 has an elliptical cross-section to allow for some constrained motion of the transition rod 446 within the rod channel 460 after implantation. The second housing 444 further includes an aperture 462 adjacent the rod channel 460 for receiving a locking element 464. The aperture 462 includes a locking element engagement feature 466 configured to engage the corresponding housing engagement feature 468 of the locking element 464. When inserted in the aperture 462, the locking element 464 is able to contact and lock in place the transition rod 446 while allowing for some controlled movement within the rod channel 460. The locking element 464 comprises a setscrew having a housing engagement feature 468 and a rod engagement surface. The housing engagement feature 468 complementarily engages the locking element engagement feature 466 of the first housing 462. The rod engagement surface is configured to engage the transition rod 446 and may be planar, convex, or concave.

The pivot connector 448 comprises a generally cylindrical member including a first end flange 470, a second end flange 472, and a central flange 474. The first end flange 470 is configured to be received within a recess 476 formed in the first housing 442. The second end flange 472 is configured to be received within a recess 478 formed in the second housing 444. The central flange 474 is positioned between the first and second housings 442, 444 when assembled and acts as a washer. The first and second housings 442, 444 are allowed to pivot relative to one another. This pivoting ability may be controlled or partially restricted but is not locked.

Figure 62:
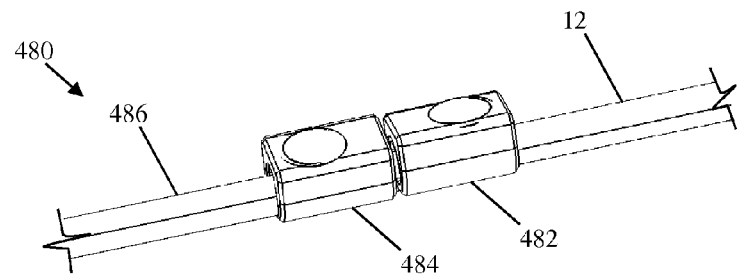
FIG. 62 is a perspective view of another example of a transition apparatus suitable for use with the vertebral fixation system of FIG. 1.
Figure 63:
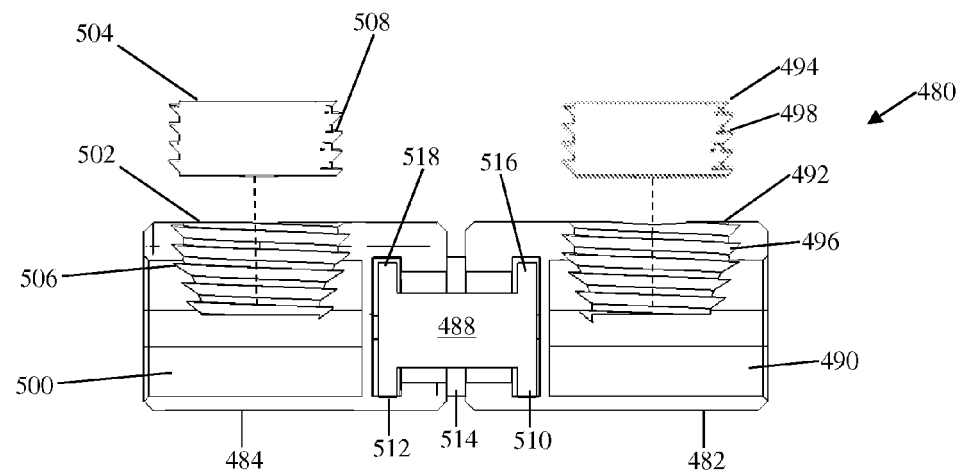
FIG. 63 is a partially exploded sectional view of the transition apparatus of FIG. 62.
Figure 64:
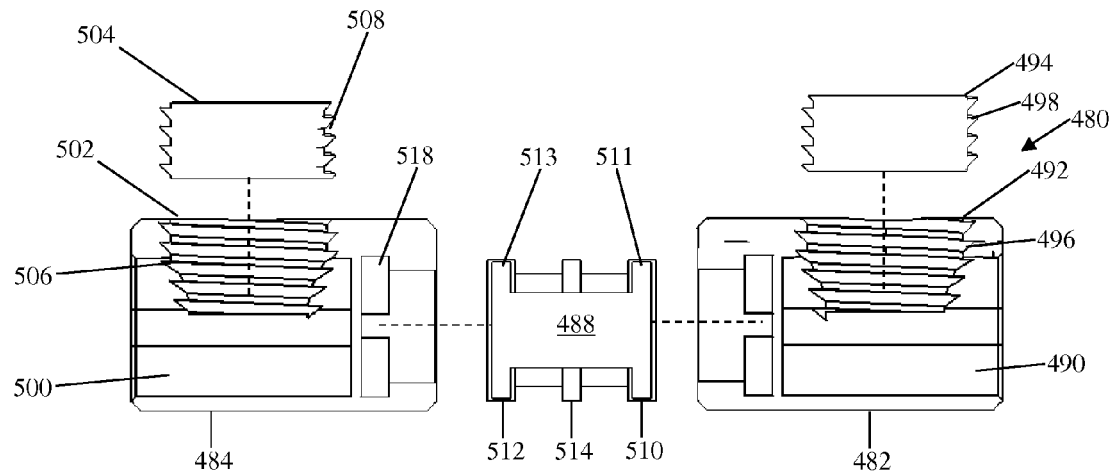
FIG. 64 is an exploded sectional view of the transition apparatus of FIG. 62.
Figure 69:
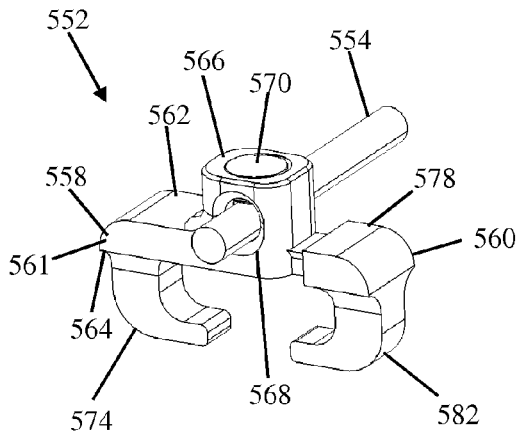
FIGS. 69 and 70 are perspective views of an example of a rib clamp forming part of a bone anchor suitable for use with the vertebral fixation system of FIG. 1.
Figure 70:
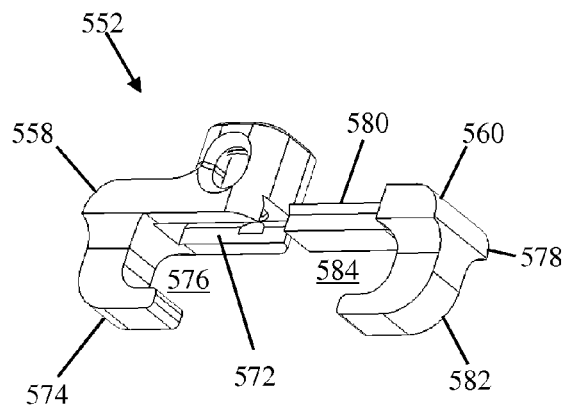
Figure 71:
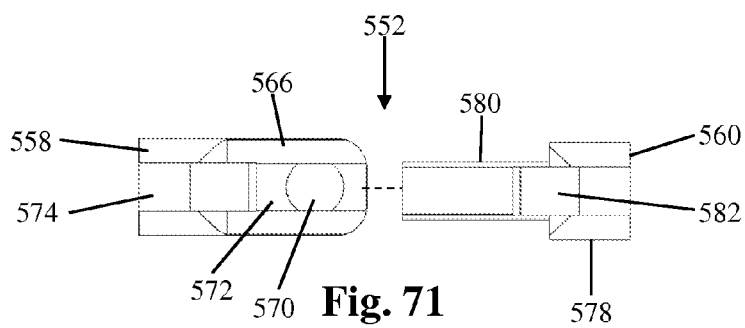
FIG. 71 is an exploded plan view of the rib clamp of FIG. 69.
Figure 72:
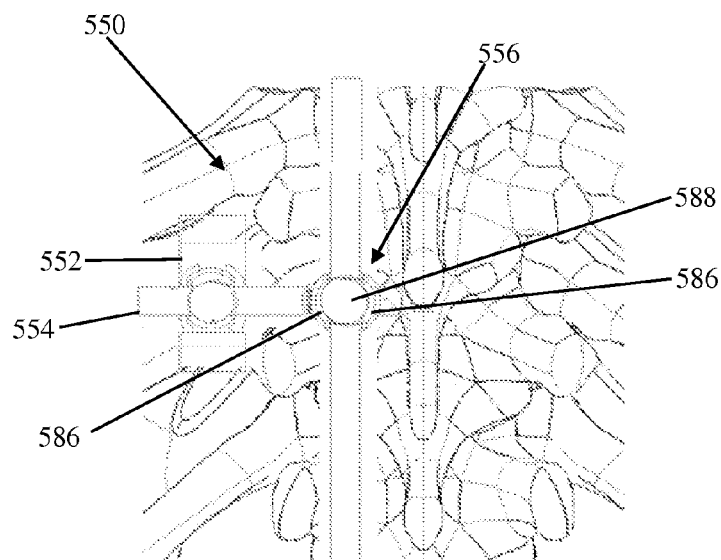
FIG. 72 is a plan view of the bone anchor of FIG. 69 implanted within a human spine.
Figure 77:
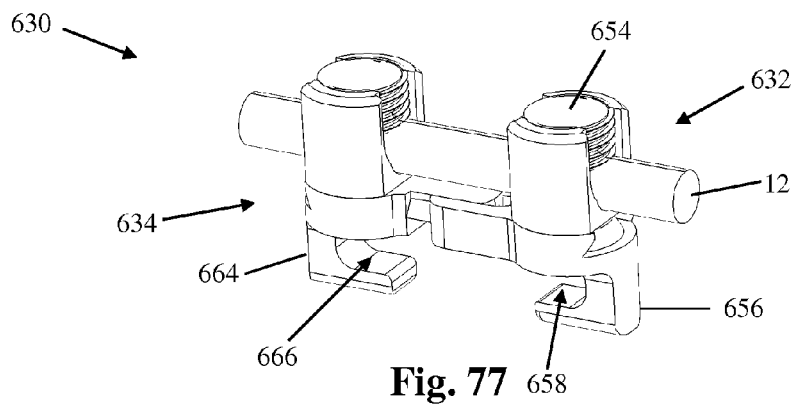
FIGS. 77 and 78 are perspective views of another example of a bone anchor forming part of the vertebral fixation system of FIG. 1.
Figure 78:
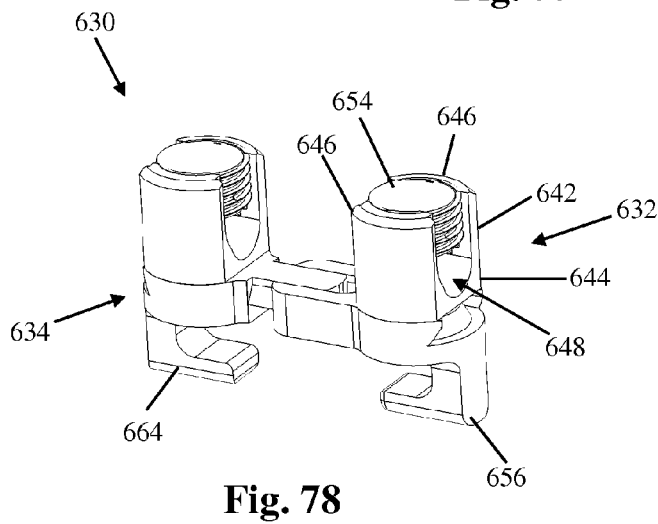
Figure 80:
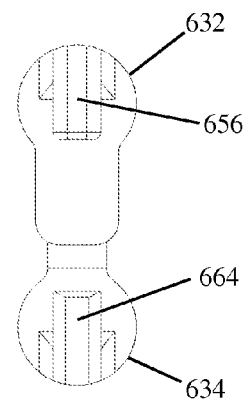
FIG. 80 is a plan view of the bone anchor of FIG. 77.
Figure 79:
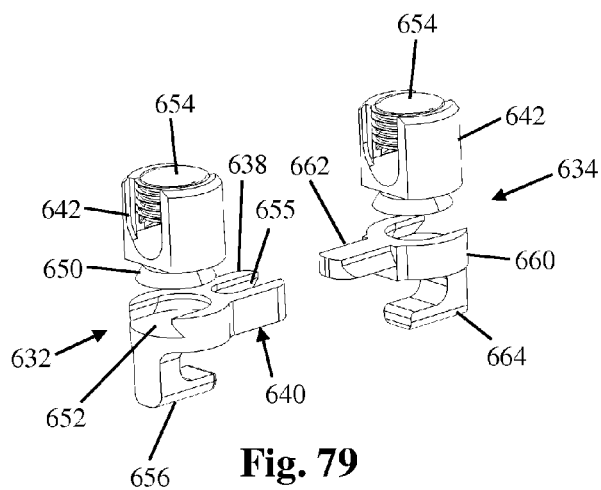
FIG. 79 is an exploded perspective view of the bone anchor of FIG. 77.
Figure 81:
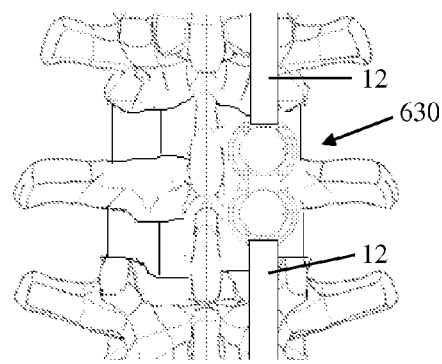
FIG. 81 is a plan view of the bone anchor of FIG. 77 implanted within a human spine.
Figure 92:
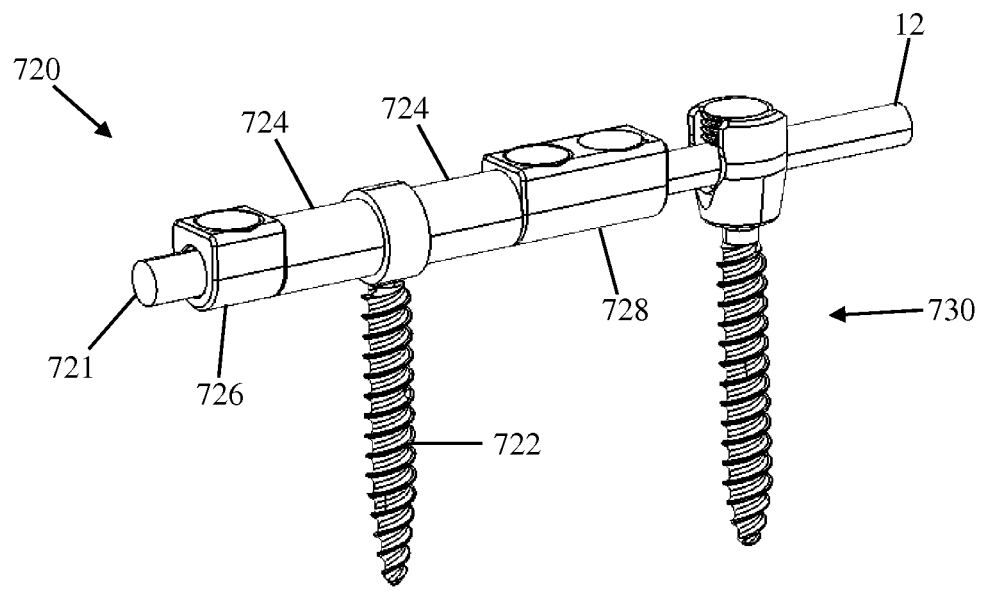
FIGS. 92 and 93 are perspective and sectional views, respectively of an example of a fixation assembly including an elastomeric bumper configured for use with the spinal fixation system of FIG. 1.
Figure 93:
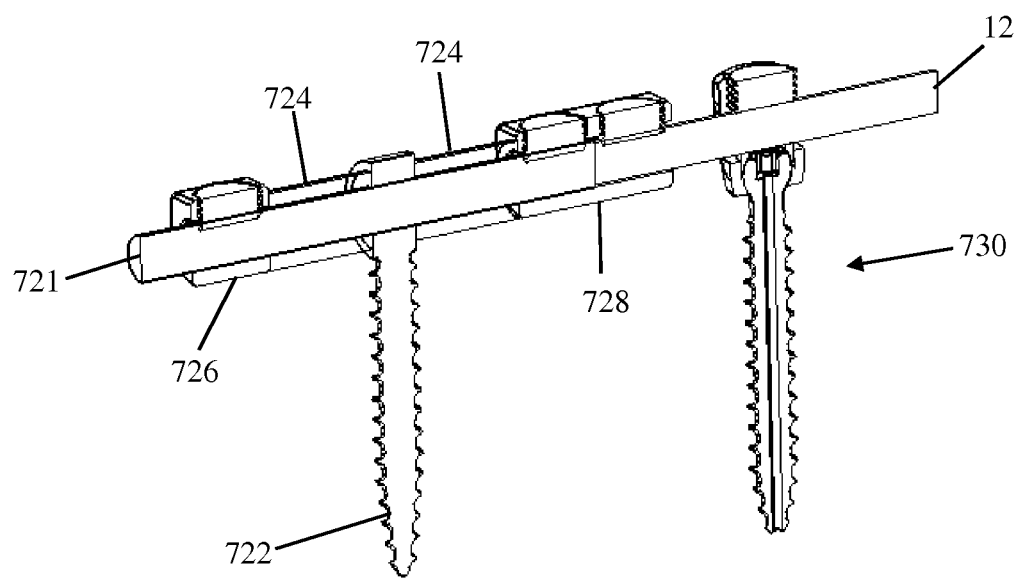
Figure 94:
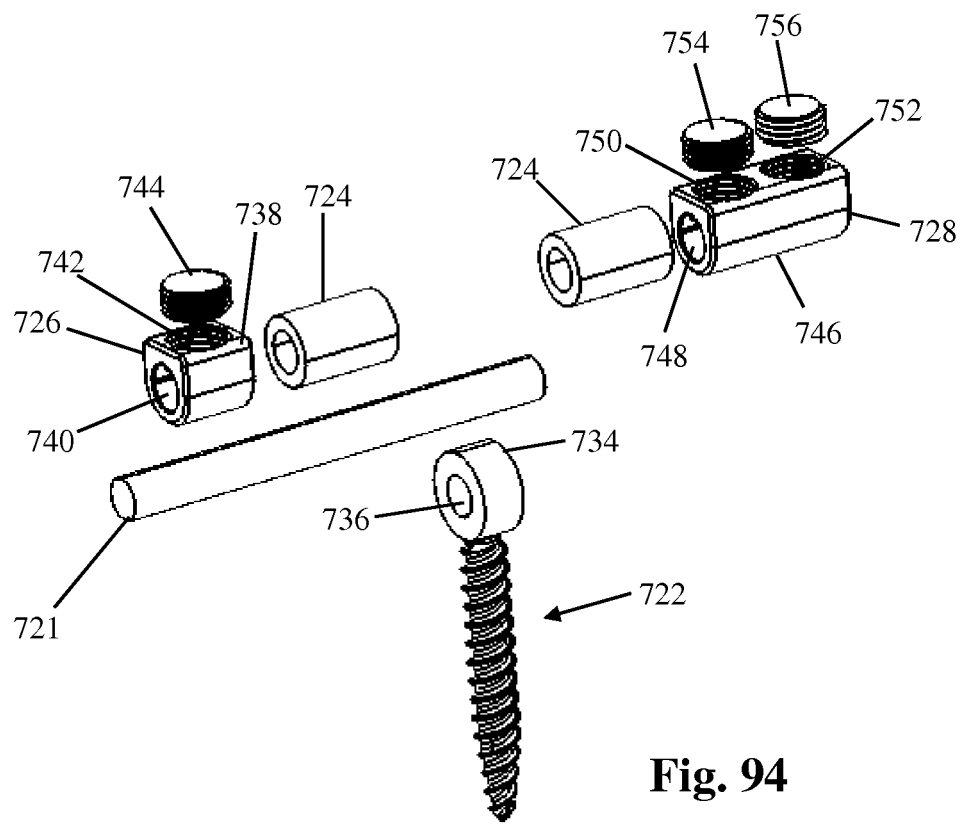
FIG. 94 is an exploded view of the fixation assembly of FIG. 92.
Figure 95:
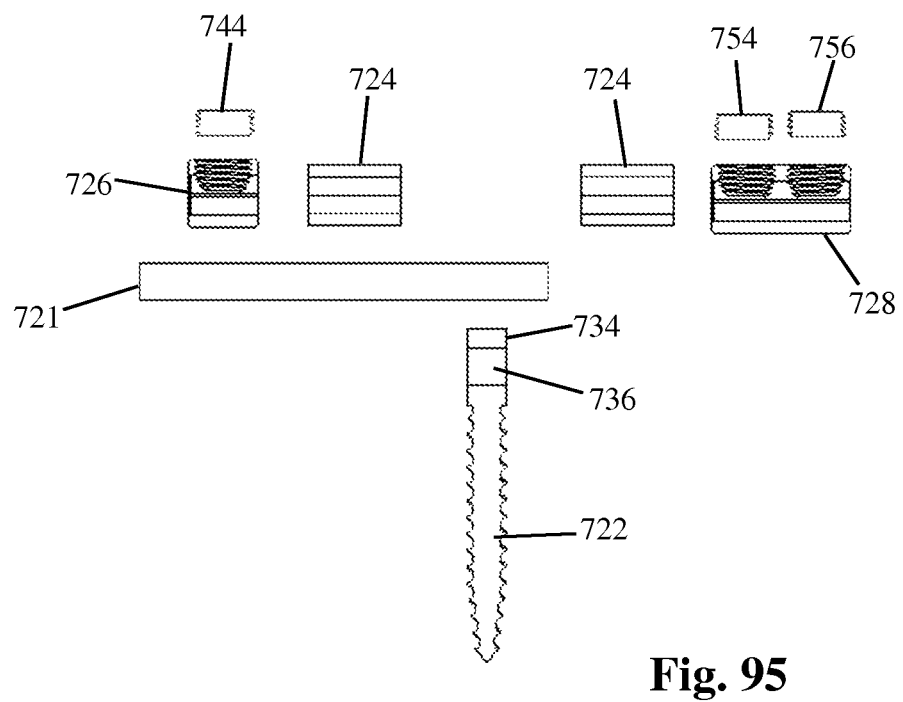
FIG. 95 is an exploded perspective view of the fixation assembly of FIG. 92.

FIGS. 62-64 illustrate another example of a transition apparatus configured for use with the vertebral fixation system 10. The transition apparatus 480 of the present example generally comprises an inline rod connector with multiple degrees of freedom of movement. The transition apparatus 480 includes a first housing 482 configured for receiving the spinal rod 12 and a second housing 484 configured for receiving a transition rod 486. The first housing 482 and second housing 484 are connected via a pivot connector 488. The first housing 482 is inline with the second housing 484 such that a longitudinal axis extending through the first rod channel 490 is axially aligned with a longitudinal axis extending through the second rod channel 500.

The first housing includes a first rod channel 490 extending therethrough that is sized and configured to receive the proximal portion of the spinal rod 12. The rod channel 490 has an elliptical cross-section to allow for some constrained motion of the spinal rod 12 within the rod channel 490 after implantation. The first housing 482 further includes an aperture 492 adjacent the rod channel 490 for receiving a locking element 494. The aperture 492 includes a locking element engagement feature 496 configured to engage the corresponding housing engagement feature 498 of the locking element 494. When inserted in the aperture 492, the locking element 494 is able to contact and lock in place the spinal rod 12 while allowing for some controlled movement within the rod channel 490. The locking element 494 comprises a setscrew having a housing engagement feature 498 and a rod engagement surface. The housing engagement feature 498 complementarily engages the locking element engagement feature 496 of the first housing 482. The rod engagement surface is configured to engage the spinal rod 12 and may be planar, convex, or concave. Although not shown, the locking element 494 may alternatively be equipped with a rod engaging insert comprising a block of elastomeric material (for example) as shown and described in various example embodiments disclosed above.

The second housing 484 includes a second rod channel 500 extending therethrough that is sized and configured to receive a distal portion of the transition rod 486. The rod channel 500 has an elliptical cross-section to allow for some constrained motion of the transition rod 486 within the rod channel 500 after implantation. The second housing 484 further includes an aperture 502 adjacent the rod channel 500 for receiving a locking element 504. The aperture 502 includes a locking element engagement feature 506 configured to engage the corresponding housing engagement feature 508 of the locking element 504. When inserted in the aperture 502, the locking element 504 is able to contact and lock in place the transition rod 486 while allowing for some controlled movement within the rod channel 500. The locking element 504 comprises a setscrew having a housing engagement feature 508 and a rod engagement surface. The housing engagement feature 508 complementarily engages the locking element engagement feature 506 of the first housing 502. The rod engagement surface is configured to engage the transition rod 486 and may be planar, convex, or concave.

The pivot connector 488 comprises a generally cylindrical member including a first end flange 510, a second end flange 512, and a central flange 514. The first end flange 510 is configured to be received within a recess 516 formed in the first housing 482. The first end flange 510 may be equipped with an elastomeric coating 511 that allows for restrained translational movement of the first end flange 510 within the recess 516. The second end flange 512 is configured to be received within a recess 518 formed in the second housing 484. The second end flange 512 may be equipped with an elastomeric coating 513 that allows for restrained translational movement of the second end flange 512 within the recess 518. The central flange 514 is positioned between the first and second housings 482, 484 when assembled and acts as a washer. The first and second housings 482, 484 are allowed to pivot relative to one another. This pivoting ability may be controlled but is not locked.

FIGS. 65-68 illustrate an example of another type of bone anchor configured for use with the vertebral fixation system 10. Generally, the bone anchor 520 is configured to attach to a bone structure (e.g. a transverse process $TP_1$ or lamina of vertebra $V_1$) without puncturing or otherwise invading the bone. The bone anchor 520 may be used with the spinal rod 12 or one of the several examples of flexible transition rod (e.g. PEEK, cable) disclosed above.

The bone anchor 520 includes a housing 522, an attachment flange 524 extending from the base of the housing 522, and a locking element 526. The housing 522 includes a pair of upstanding arms 530 separated by and forming part of a rod channel 532. The upstanding arms 530 include a locking element engagement feature 534 disposed on the interior face of each arm 530. The locking element engagement feature 534 mates with a complementary housing engagement feature 536 on the locking element 526 to secure the transition rod within the rod channel 532. The attachment flange 524 has a concave first portion 538 extending away from the housing 522 and a generally planar second portion 540 adjacent the first portion 538. The concave first portion 538 and generally planar second portion 540 together form a cavity 542 (along with the bottom face of the housing 522) dimensioned to receive a bone segment. The second portion 540 is at least slightly flexible so that it may accommodate different sizes of bone but also so that it may experience some post-surgical adjustment without dislodging from the bone. This flexibility may be achieved by varying the thickness of the material or by using more flexible/elastic materials in the manufacture of the flange 524. By way of example only, the bone anchor 520 of the present example is sized and configured to be used with transverse process bone, however other configurations are possible.

At least one of the upstanding arms 530 includes a tether connector 544 extending outwardly away from the arm 530 and configured to fixedly receive a tether 546 therein. By way of example, the tether connector 544 comprises a post member having a lumen 545 formed therein that is sized to receive at least a portion of the tether 546. The tether 546 may be formed of any material suitable for medical use, including but not limited to allograft tendon, autograft tendon, braided polyethylene, PEEK, or PEKK. In some instances the tether 546 may be formed of elastic material. The tether 546 may be formed of any length necessary to secure the bone anchor 520 to surrounding bone by wrapping around the bone. The tether 546 of the instant example has a stop element 548 is attached to or otherwise forms the proximal end of the tether 546. The stop element 548 buffers against the tether connector 544 and acts as a physical barrier to prevent the proximal end of the tether 546 from passing through the lumen 545. In this way the tether 546 is secured to the tether connector 544. Other attachment methods of securing the tether 546 to the tether connector 544 are possible, including but not limited to adhesive, spot welding, and the like.

The locking element 526 may be any of the previously described locking element examples disclosed herein. The locking element 526 may or may not be equipped with a block of elastomeric material, depending on the type of rod element that is secured in the rod channel 532 by the locking element 526.

FIGS. 69-72 illustrate another example of a non-screw bone anchor configured for use with the vertebral fixation system 10. The bone anchor 550 of the instant example generally comprises a clamp-type mechanism suitable for attachment to a rib bone. The bone anchor 550 has includes a rib clamp 552, a connecting rod 554, and a rod connector 556. The rib clamp 552 includes a first clamp member 558 and a second clamp member 560 that are translationally connected to each other.

The first clamp member 558 has an elongated generally rectangular base 561 having a top side 562 and a bottom side 564. The top side 562 has a housing 566 positioned on a first end of the base 561 and protruding away from the top side 562. The housing 566 includes a rod hole 568 configured to receive the connecting rod 554 and a locking element 570 for securing the connecting rod 554 to the housing 566. The bottom side 564 includes an elongated translation recess 572 and a curved flange 574. The translation recess 572 is formed within the bottom side 564 on the first end of the base 561 (underneath the housing 566) and is configured to slideably receive the translation arm 580 of the second clamp member 560. The curved flange 574 is positioned on the second end of the base 561 and extends away from the bottom side 564 before curving inward (i.e. toward the second clamp member 560). The bottom side 564 and curved flange 574 together form a cavity 576 sized and configured to receive at least a portion of a rib bone.

The second clamp member 560 includes a base 578 and a translation arm 580 extending laterally from the base 578. The translation arm 580 mates with the translation recess 572 of the first clamp member 558 and is capable of translation within the recess to allow the rib clamp 552 to be secured to a bone. The second clamp member 560 further includes a curved flange 582 that extends away from the bottom side of the second clamp member 560 before curving inward (i.e. toward the first clamp member 558). The translation arm 580 and curved flange 582 together from a cavity 584 sized and configured to receive at least a portion of a rib bone.

The rod connector 556 has a base and a pair of upstanding arms 586 that define a rod channel in between. The rod channel is configured to receive the spinal rod 12 or a transition rod (e.g. any of the transition rod types described herein). The rod connector 556 further has a locking element 588 (e.g. any of the locking elements described herein) configured to secure the rod connector 556 to the spinal rod 12 (or transition rod). The connecting rod 554 extends laterally from one of the upstanding arms 586.

The bone anchor 550 has multiple articulating connections to help absorb force and allow controlled movement after implantation. One articulating connection is between the rod connector 556 and the spinal rod 12. This is much the same as the interaction between the spinal rod and various examples of bone screws described above. Another articulating connection is between the connecting rod 554 and the rib clamp 552. Thus slight shifting can occur without causing dislodgement of the bone anchor 550.

FIGS. 73-76 illustrate an alternative example of a rib clamp for use with the bone anchor 550. The rib clamp 590 of the instant example is substantially similar to the rib clamp 552 described above with the significant difference being the moveable housing 595 as will be described below. The rib clamp 590 includes a first clamp member 592 and a second clamp member 594 that are translationally connected to each other, and a housing 595 for receiving the connecting rod 554.

The first clamp member 592 has an elongated generally rectangular base 596 having a top side 598 and a bottom side 599. The top side 598 has a pedestal 600 positioned on a first end of the base 596 and protruding away from the top side 598. The pedestal 600 includes a first translation recess 602 having a length dimension extending parallel to the longitudinal axis of the rib clamp 590. The first translation recess 602 is configured to receive the lower flange 610 of the housing 595. The housing 595 has a base 604 and a pair of upstanding arms 606 separated by and partially defining a rod channel 608 sized and configured to receive the connecting rod 554 therein. The housing 595 further includes a lower flange 610 that slideably mates with the first translation recess 602 to connect the housing 595 to the first clamp member 592. A locking element 612 (e.g. any of the set-screw style locking elements described herein) mates with the housing 595 to secure the connecting rod 554 to the housing 595.

The bottom side 599 includes an elongated translation recess 614 and a curved flange 616. The translation recess 614 is formed within the bottom side 599 on the first end of the base 596 (underneath the housing 566) and is configured to slideably receive the translation arm 580 of the second clamp member 594. The curved flange 616 is positioned on the second end of the base 596 and extends away from the bottom side 599 before curving inward (i.e. toward the second clamp member 594). The bottom side 599 and curved flange 616 together form a cavity 618 sized and configured to receive at least a portion of a rib bone.

The second clamp member 594 includes a base 620 and a translation arm 622 extending laterally from the base 620. The translation arm 622 mates with the translation recess 614 of the first clamp member 592 and is capable of translation within the recess to allow the rib clamp 590 to be secured to a bone. The second clamp member 594 further includes a curved flange 624 that extends away from the bottom side of the second clamp member 594 before curving inward (i.e. toward the first clamp member 592). The translation arm 622 and curved flange 624 together from a cavity 584 sized and configured to receive at least a portion of a rib bone.

The rod connector 556 has a base and a pair of upstanding arms 586 that define a rod channel in between. The rod channel is configured to receive the spinal rod 12 or a transition rod (e.g. any of the transition rod types described herein). The rod connector 556 further has a locking element 588 (e.g. any of the locking elements described herein) configured to secure the rod connector 556 to the spinal rod 12 (or transition rod). The connecting rod 554 extends laterally from one of the upstanding arms 586.

The bone anchor 550 has multiple articulating connections to help absorb force and allow controlled movement after implantation. One articulating connection is between the rod connector 556 and the spinal rod 12. This is much the same as the interaction between the spinal rod and various examples of bone screws described above. Another articulating connection is between the connecting rod 554 and the rib clamp 590. Thus slight shifting can occur without causing dislodgement of the bone anchor 550.

FIGS. 77-81 illustrate another example of a non-screw bone anchor configured for use with the vertebral fixation system 10. The bone anchor 630 of the instant example generally comprises a clamp-type mechanism suitable for attachment to a lamina or transverse process or spinous process bone or a combination thereof. The bone anchor 630 includes a first clamp member 632 and a second clamp member 634 that are translationally mated with each other.

The first clamp member 632 has an elongated base 636 having a top side 638 and a bottom side 640. The top side 638 has a housing 642 positioned on a first end of the base 636 and protruding away from the top side 638. The housing 642 has a base 644 and a pair of upstanding arms 646 separated by and partially defining a rod channel 648 sized and configured to receive the spinal rod 12 (or transition rod) therein. By way of example, the housing 642 further includes a lower flange 650 that mates with a first recess 652 formed in the top side 638 to connect the housing 642 to the first clamp member 632. A locking element 654 (e.g. any of the setscrew style locking elements described herein) mates with the housing 642 to secure the rod 12 to the housing 642. The top side 638 further includes a second recess 655 formed on the second end of the base 636 configured to slideably receive the translation arm 662 of the second clamp member 634. The bottom side 640 includes a flange 656 positioned on the first end of the base 636 (underneath the housing 642) and extending away from the bottom side 640 before curving inward (i.e. toward the second clamp member 634). The bottom side 640 and flange 656 together form a cavity 658 sized and configured to receive at least a portion of a lamina or transverse process bone.

The second clamp member 634 includes a base 660 and a translation arm 662 extending laterally from the base 660. The translation arm 662 mates with the second recess 655 of the first clamp member 632 and is capable of translation within the recess to allow the bone anchor 630 to be secured to a bone. The second clamp member 634 also includes a housing 642 with locking element 654 that are identical to the same elements described in relation to the first clamp member 632. The second clamp member 634 further includes a flange 664 that extends away from the bottom side of the second clamp member 634 before curving inward (i.e. toward the first clamp member 632). The translation arm 662 and flange 664 together from a cavity 666 sized and configured to receive at least a portion of a lamina or transverse process bone.

The prior examples described herein have sought to address the need for reducing or preventing the occurrence of junctional disease and failures through instrumentation that aims to alleviate stress on the proximal and/or distal termini of multi-level spinal fixation systems. Another way to limit flexion in the proximal and/or distal instrumented vertebrae is to create physical barriers or countermeasures that either prevent or exert a counterforce to reverse the kyphosis. One example of such a physical barrier is a rod bumper that may be inserted between a bone anchor and spinal rod, and extends a short distance distally along the spinal rod. As flexion associated with kyphosis occurs and the upper vertebra falls forward, the bumper pushes backwards on the spinal rod. In response, the spinal rod exerts a return force on the bumper, which then causes the upper vertebra to return to a more normal position. FIGS. 82-86 illustrate one example of a bone anchor 670 with associated rod bumper 672 that may be employed as a terminal anchor in a fixation construct. The bone anchor 670 is shown by way of example as a pedicle screw with a tulip and lock screw, however the rod bumper may be used with other fixation hardware.

By way of example, the bone anchor 670 includes a housing 674, threaded shank 676, and locking element 678. The housing has a base 680 and a pair of upstanding arms 682 that form the rod channel. The locking element 678 may be any of the previously described examples of locking elements. A rod bumper 672 may be attached to the housing 674 or one end of may be inserted into the rod channel between the housing 674 and spinal rod 12. The rod bumper 672 has a concave rod engaging surface 684 so as to reduce the profile of the spinal fixation system after implantation and prior to the occurrence of flexion.

FIGS. 87-91 illustrate another example of a bone anchor and rod bumper combination configured for use with cords or other non-traditional transition rods. The bone anchor 690 is shown by way of example as a pedicle screw with a tulip and lock screw, however the rod bumper may be used with other fixation hardware.

By way of example, the bone anchor 690 includes a housing 692, threaded shank 694, and locking element 696. The housing has a base 698 and a pair of upstanding arms 700 that form the rod channel. The locking element 696 may be any of the previously described examples of locking elements. A rod bumper 702 may be attached to the housing 692 or one end of may be inserted into the rod channel between the housing 692 and transition cable rod 701. The rod bumper 702 is has an elongated body 704 with a concave rod engaging surface 706 to reduce the profile of the spinal fixation system after implantation and prior to the occurrence of flexion. The rod bumper 702 further includes a distal housing 708 to capture the transition cable rod 701 therein. The distal housing 708 is necessary to ensure the transition cable rod 701 remains aligned with the rod bumper 702 given the flexibility of the transition cable rod 701. The distal housing 708 is similar to the previously described examples of housings in that it has a base 710 and a pair of upstanding arms 712 that act in concert to form a rod channel 714. A locking element 716 may also be included to ensure the transition cable rod 701 remains in the rod channel 714. The locking element 716 may be any of the previously described examples of locking elements. Although described herein with regard to this specific example, other configurations are possible. For example the distal housing 708 may be replaced by a loop that achieves the goal of keeping the transition cable rod 701 aligned with the rod engaging surface 706.

FIGS. 92-95 illustrate an example of another fixation assembly that works to counteract flexion at the proximal and/or distal instrumented vertebra. The fixation assembly 720 described herein forms part of the spinal fixation system 10 and is suitable for use with the spinal rod 12 and/or a transition rod 721 such as one of the several examples described above. By way of example, the fixation assembly 720 is described herein as being used with both the spinal rod 12 and a transition rod 721. The fixation assembly 720 includes a first bone anchor 722, a pair of elastomeric sheaths 724, and first and second locking rings 726, 728. The present example is shown and described with a second bone anchor 730 associated with the spinal rod 12 and implanted at an adjacent vertebral level.

The first bone anchor 722 may be any bone anchor suitable for securing a spinal rod in place relative to a bone. By way of example, the bone anchor 722 includes a threaded shank 732 and a ring shaped head 734. Other types of anchors including tulip based pedicle screws like those described in above examples (as well as bone anchor 730 of this example) are possible. The threaded shank 732 is configured to provide purchase in bone tissue. The ring shaped head 734 includes a rod hole 736 sized and configured to allow passage of the transition rod 721 (or spinal rod 12) therethrough. One elastomer sleeve 724 is positioned on the rod 721 proximally of the head 734, and the other elastomer sleeve 724 is positioned on the rod 721 distally of the head 734. The first locking ring 726 is secured to the rod 721 proximally of the proximal elastomer sleeve 724. The second locking ring 728 is secured to the rod 721 distally of the distal elastomer sleeve 724.

The first locking ring 726 shown by way of example comprises a body 738 having a rod hole 740 extending therethrough and a locking element aperture 742 that opens to the rod hole 740 and is configured to receive a locking element 744. The locking element 744 may be any of the setscrew type locking elements described by way of example above. Other locking ring configurations are possible that may or may not need secondary locking elements.

The second locking ring 728 shown by way of example is capable of joining a pair of rods and comprises a body 746 having a rod hole 748 extending therethrough, and first and second locking element apertures 750, 752 that open to the rod hole 748 and are configured to receive first and second locking elements 754, 756 respectively. The locking elements 754, 756 may be any of the setscrew type locking elements described by way of example above. In the instant example the first locking element 754 secures the second locking element 728 to the transition rod 721 and the second locking element 756 secures the second locking element 728 to the spinal rod 12. Although described as a junction point between the transition rod 721 and the spinal rod 12, the second locking ring 728 may be secured to only one rod and therefore may be identical to the first locking ring 726. Other locking ring configurations are possible that may or may not need secondary locking elements.

In an initial unbiased position, the various elements are positioned such that the proximal elastomer sleeve 724 abuts the head 734 and first locking ring 726, while the distal elastomer sleeve 724 abuts the head 734 and second locking ring 726. When flexion occurs and the rod 721 experiences forward bending, the elastomer sleeves 724 will be compressed and as a result exert a counterforce back on the first and second locking rings 726, 728 and head 734. This counterforce will work to return the rod 721 toward its initial position.

Figure 96:
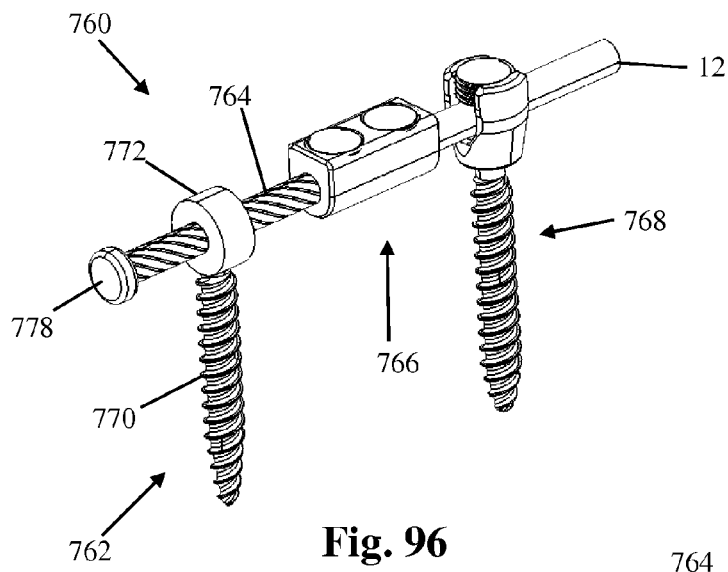
FIGS. 96 and 97 are perspective and sectional views, respectively, of another example of a fixation assembly including cable and a flexion stop configured for use with the spinal fixation system of FIG. 1.
Figure 97:
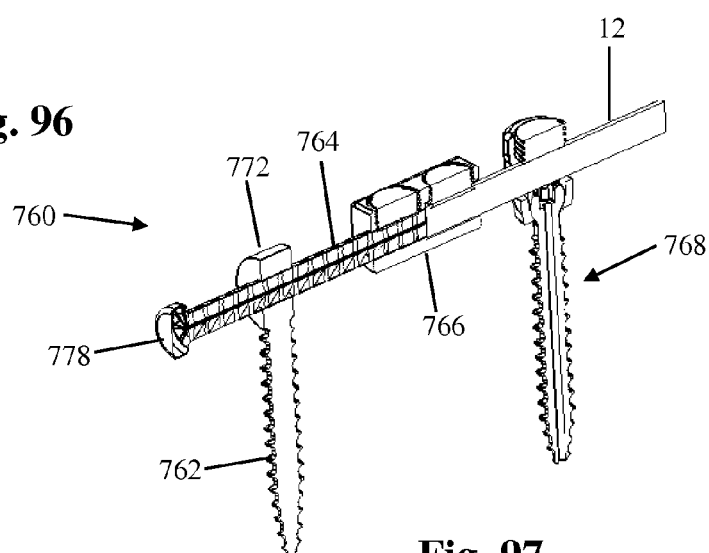
Figure 98:
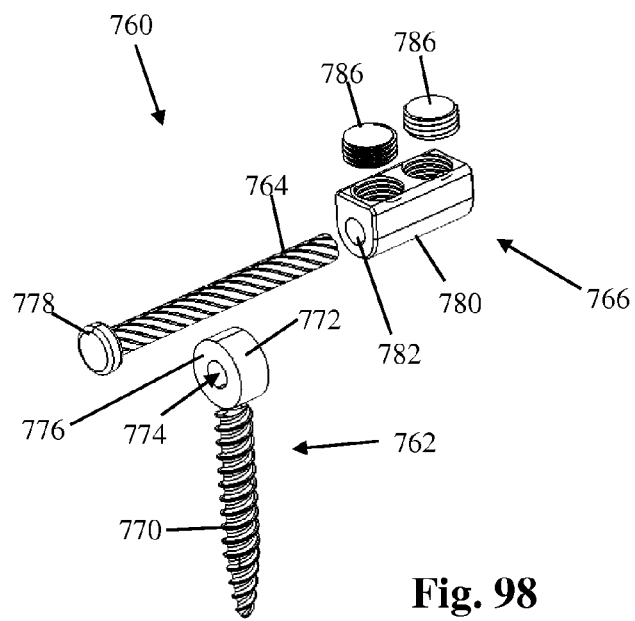
FIG. 98 is an exploded view of the fixation assembly of FIG. 96.

FIGS. 96-98 illustrate an example of another fixation assembly that works to present a physical barrier to flexion at the proximal and/or distal instrumented vertebra. The fixation assembly 760 described herein forms part of the spinal fixation system 10 and is suitable for use with the spinal rod 12 and/or a transition rod such as one of the several examples described above. By way of example, the fixation assembly 760 includes bone anchor 762, flexible cable rod 764, and attachment element 766. The present example is shown and described with a second bone anchor 768 associated with the spinal rod 12 and implanted at an adjacent vertebral level.

The bone anchor 762 may be any bone anchor suitable for securing a spinal rod in place relative to a bone. By way of example, the bone anchor 762 includes a threaded shank 770 and a ring shaped head 772. Other types of anchors including tulip based pedicle screws like those described in above examples (as well as bone anchor 768 of this example) are possible. The threaded shank 770 is configured to provide purchase in bone tissue. The ring shaped head 772 includes a rod hole 774 sized and configured to allow passage of the cable rod 764 therethrough. The head 772 further includes a proximal abutment surface 776 oriented toward the proximal end of the cable rod 764 and configured to flushly engage the flexion stop 778 when necessary during flexion.

The cable rod 764 is a flexible cable and has a proximal terminus comprising a flexion stop 778. By way of example, the flexion stop 778 is a rigid member attached to the end of the cable rod 764 and having a diameter (or length dimension) that is greater than the diameter of the rod hole 774 so that the flexion stop 778 is incapable of passing through the rod hole 774. During flexion the cable rod 764 will be pulled through the rod hole 774 until the flexion stop 778 abuts the abutment surface 776. When this abutment happens, the top vertebra (that is falling forward) will in effect be held up by the cable rod 764, preventing further flexion from occurring.

The attachment element 766 is configured to attach the distal end of the cable rod 764 to the proximal end of the spinal rod 12. By way of example, the attachment element 766 comprising a housing 780 having a rod channel 782 and a plurality of locking element apertures 784, each of which is configured to receive a locking element 786. In use, the distal end of the cable rod 764 is received within the rod channel 782 and secured with the proximal most locking element 786. The proximal end of the spinal rod 12 is received within the rod channel 782 and secured with the distal most locking element 786. In the present example, the locking elements 786 may be one of the several examples of setscrew type locking elements described above. Although shown and described herein as a housing and setscrew based attachment mechanism, it should be understood that the cable rod 764 and spinal rod 12 may be joined by any suitable method without departing from the scope of this disclosure.

Several of the examples described herein involve tethers attached to the bone anchor or to a bone hook that then act as artificial ligaments to secure the rod to the bone. In some instances it may not be necessary to attach the tethers to implanted hardware other than the rod. In these instances it is contemplated that the tether may be wrapped around the bone structure without having a terminus that is attached to implanted hardware.

While specific embodiments have been shown by way of example in the drawings and described herein in detail, it will be appreciated that the invention is susceptible to various modifications and alternative forms (beyond combining features disclosed herein). The description herein of specific embodiments is not intended to limit the invention to the particular forms disclosed, but on the contrary, the invention is to cover all modifications, equivalents, and alternatives falling within the spirit and scope of the invention.

What is claimed is:

1. A method for preventing the onset of junctional joint disease subsequent to implantation of a spinal fixation construct to fix two or more segments of the spine together during an index surgery, the method comprising the steps of:
    anchoring a first bone anchor through a pedicle of a first vertebra, the bone anchor including a threaded shank and a housing, the housing having a base connected to the shank and a pair of upstanding spaced apart arms forming a channel dimensioned to fit a portion of a connecting rod therein;
    anchoring a second bone anchor through a pedicle of a second vertebra situated superior to the first vertebra, the second bone anchor including a threaded shank and a housing, the housing having a base connected to the shank and a pair of upstanding spaced apart arms forming a channel dimensioned to fit a portion of the connecting rod therein;
    anchoring a third bone anchor through a pedicle of a third vertebra situated superior to the second vertebra, the third bone anchor including a threaded shank and a housing, the housing having a base connected to the shank and a pair of upstanding spaced apart arms forming a channel dimensioned to fit a portion of the connecting rod therein;
    locking a rigid connecting rod within each of the first second and third bone anchor housings, the pair of upstanding arms of the first bone anchor being mateable with a first locking element that locks the rigid connecting rod to the first bone anchor to create a first connection, the pair of upstanding arms of the second bone anchor being mateable with a second locking element that locks the rigid connecting rod to the second bone anchor to create a second connection, and the pair of upstanding arms of the third bone anchor being mateable with a third locking element that locks the rigid connecting rod to the third bone anchor to create a third connection, wherein the first connection is a rigid connection, the second connection is a rigid connection, and the third connection is a compliant connection;
    wherein the third bone anchor housing is coupled to the shank in a multi-axial configuration in which the housing can initially rotate and pivot relative to the shank prior to locking the rod within the housing; and
    wherein the third bone anchor further includes a collar situated around the shank and flushly engaged with the housing base, the collar being formed of elastomeric material to provide the compliant connection, wherein the collar further includes a spring disposed therein.

2. The method of claim 1, wherein the spring is biased toward the housing.

3. The method of claim 1, the method further comprising the step of:
    coupling a tether to a fourth vertebra situated superior to the third vertebra, the tether being attached to one or more of the first bone anchor, the second bone anchor, the third bone anchor, and the rigid connection rod.

4. The method of claim 3, wherein the tether is formed of plastic fibers.

5. The method of claim 4, wherein the plastic fibers are braided.

6. The method of claim 5, wherein the plastic fibers are polyethylene.

7. The method of claim 3, wherein coupling the tether to the fourth vertebra includes wrapping the tether around one or more of the transverse process, lamina, rib, and spinous process of the fourth vertebra.

8. The method of claim 7, wherein after the tether is wrapped around one or more of the transverse process, lamina, rib, and spinous process, the tether is attached back to itself.

9. The method of claim 7, wherein after the tether is wrapped around one or more of the transverse process, lamina, rib, and spinous process, the tether is attached to a fourth bone anchor anchored to the contralateral side of the third vertebra.

10. The method of claim 7, wherein coupling the tether to the fourth vertebra includes passing an anchor through the tether and engaging the anchor to one of the transverse process, lamina, rib, and spinous process of the fourth vertebra.

11. A method for preventing the onset of junctional joint disease subsequent to implantation of a spinal fixation construct to fix two or more segments of the spine together during an index surgery, the method comprising the steps of:
    anchoring a first bone anchor through a pedicle of a first vertebra, the bone anchor including a threaded shank and a housing, the housing having a base connected to the shank and a pair of upstanding spaced apart arms forming a channel dimensioned to fit a portion of a connecting element therein;
    anchoring a second bone anchor through a pedicle of a second vertebra situated superior to the first vertebra, the second bone anchor including a threaded shank and a housing, the housing having a base connected to the shank and a pair of upstanding spaced apart arms forming a channel dimensioned to fit a portion of the connecting rod therein;
    coupling a first hook to a third vertebra situated superior to the second vertebra, the first hook including a housing having a channel dimensioned to fit a portion of the connecting element therein;
    coupling a second hook to a fourth vertebra situated superior to the third vertebra, the second hook including a housing having a channel dimensioned to fit a portion of the connecting element therein;
    locking a connecting element within each of the first bone anchor housing, second bone anchor housing, first hook, and second hook, the connecting element having a first segment situated between the first bone anchor and the second bone anchor, the first segment being rigid, the connecting element having a second segment situated between the first hook and the second hook, the second segment being flexible, and the connecting element having a third segment situated between the second bone anchor and the first hook, the third segment including a transition from the rigid first segment to the flexible second segment; and wherein the first hook is engaged to a rib attached to the third vertebra and the second hook is engaged to a rib attached to the fourth vertebra.

12. The method of claim 11, the method further comprising the step of:
coupling a tether to a fourth vertebra situated superior to the third vertebra, the tether being attached to one or more of the first bone anchor, the second bone anchor, the first hook, the second hook, and the connecting element.

13. The method of claim 12, wherein the tether is formed of plastic fibers.

14. The method of claim 13, wherein the plastic fibers are braided.

15. The method of claim 14, wherein the plastic fibers are polyethylene.

16. The method of claim 12, wherein the coupling the tether to the fourth vertebra includes wrapping the tether around one or more of the transverse process, lamina, rib, and spinous process of the fourth vertebra.

17. The method of claim 16, wherein after the tether is wrapped around one or more of the transverse process, lamina, rib, and spinous process, the tether is attached back to itself.

18. The method of claim 16, wherein after the tether is wrapped around one or more of the transverse process, lamina, rib, and spinous process, the tether is attached to a fourth bone anchor anchored to the contralateral side of the third vertebra.

19. The method of claim 16, wherein coupling the tether to the fourth vertebra includes passing an anchor through the tether and engaging the anchor to one of the transverse process, lamina, rib, and spinous process of the fourth vertebra.

* * * * *